United States Patent
Wang

(10) Patent No.: US 8,628,475 B2
(45) Date of Patent: Jan. 14, 2014

(54) HYPERECHOGENIC NEEDLES

(75) Inventor: Clement D. Wang, Fishers, IN (US)

(73) Assignee: CDW Investments, LLC, Fishers, IN (US)

( * ) Notice: Subject to any disclaimer, the term of this patent is extended or adjusted under 35 U.S.C. 154(b) by 160 days.

(21) Appl. No.: 13/166,383

(22) Filed: Jun. 22, 2011

(65) Prior Publication Data

US 2011/0319758 A1 Dec. 29, 2011

Related U.S. Application Data

(60) Provisional application No. 61/398,379, filed on Jun. 24, 2010.

(51) Int. Cl.
*A61B 8/14* (2006.01)

(52) U.S. Cl.
USPC ........... 600/458; 600/459; 600/462; 600/463; 600/464; 600/561; 600/562; 600/564

(58) Field of Classification Search
USPC ......... 600/458, 459, 462, 463, 464, 561, 562, 600/564
See application file for complete search history.

(56) References Cited

U.S. PATENT DOCUMENTS

| | | | | |
|---|---|---|---|---|
| 1,822,330 | A * | 9/1931 | Ainslie | .......................... 606/145 |
| 4,277,367 | A | 7/1981 | Madsen et al. | |
| 4,401,124 | A | 8/1983 | Guess et al. | |
| 5,054,310 | A | 10/1991 | Flynn | |
| 5,289,831 | A | 3/1994 | Bosley | |
| 5,820,554 | A | 10/1998 | Davis et al. | |
| 5,921,933 | A | 7/1999 | Sarkis et al. | |
| 6,053,870 | A | 4/2000 | Fulton, III | |
| 6,306,094 | B1 | 10/2001 | Joseph | |
| 6,610,016 | B1 | 8/2003 | Violante et al. | |
| 6,860,856 | B2 | 3/2005 | Ward et al. | |
| 7,014,610 | B2 | 3/2006 | Koulik | |
| 7,229,413 | B2 | 6/2007 | Violante et al. | |
| 7,799,022 | B2 | 9/2010 | Fernald et al. | |
| 8,262,684 | B2 * | 9/2012 | List | ............................... 606/181 |
| 2003/0009100 | A1 | 1/2003 | Derendorf | |
| 2003/0028154 | A1 * | 2/2003 | Ross | .............................. 604/272 |

(Continued)

FOREIGN PATENT DOCUMENTS

| | | |
|---|---|---|
| EP | 1 118 337 | 7/2001 |
| EP | 0 941 128 | 10/2004 |
| WO | WO 2008/005669 | 1/2008 |

OTHER PUBLICATIONS

International Search Report and Written Opinion of the International Searching Authority, PCT/US2011/041457, Sep. 15, 2011, CDW Investments, LLC.

*Primary Examiner* — Sean Dougherty
(74) *Attorney, Agent, or Firm* — Krieg DeVault LLP

(57) ABSTRACT

A hyperechogenic needle includes a rigid shaft, which can be a hollow metal cannula, having a hyperechogenic particulate material affixed on an outer surface of the shaft that provides for visualization of the needle in two-dimensional (2D) ultrasound, particularly when the needle is in a position forming a non-90° angle between the longitudinal axis and the direction of the ultrasound waves in the two-dimensional ultrasound plane. The hyperechogenic particulate material can be covered by a polymeric coating or embedded in a polymeric material to provide a hyperechogenic layer. The polymeric coating and polymeric material can be electrically non-conductive or electrically conductive.

27 Claims, 17 Drawing Sheets

(56) References Cited

U.S. PATENT DOCUMENTS

| | | |
|---|---|---|
| 2004/0073158 A1 | 4/2004 | Shah |
| 2004/0186340 A1 | 9/2004 | Reed |
| 2004/0260269 A1 | 12/2004 | Assaf |
| 2007/0179508 A1 | 8/2007 | Arndt |
| 2008/0125800 A1* | 5/2008 | List .............................. 606/181 |
| 2009/0005774 A1 | 1/2009 | Fernald |
| 2009/0318746 A1 | 12/2009 | Thurmond, II |
| 2011/0009862 A1 | 1/2011 | Fernald et al. |
| 2011/0319758 A1* | 12/2011 | Wang ........................... 600/439 |
| 2012/0302950 A1* | 11/2012 | Landsman et al. ......... 604/95.05 |

* cited by examiner

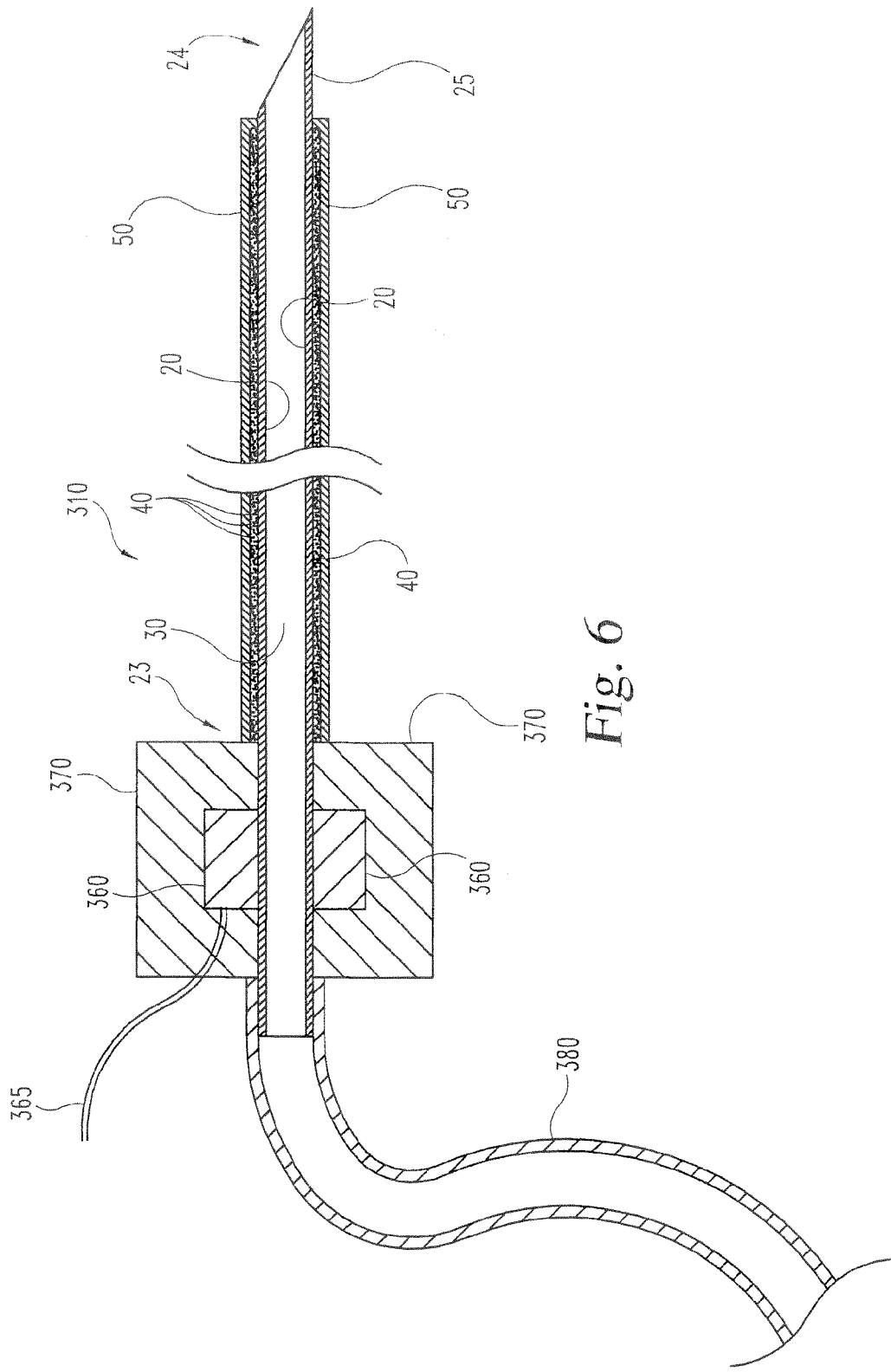

HYPERECHOGENIC NEEDLES

CROSS REFERENCE TO RELATED APPLICATION

The present application claims the benefit of U.S. Provisional Patent Application No. 61/398,379 filed 24 Jun. 2010, which is incorporated herein by reference in its entirety.

FIELD OF THE INVENTION

This invention is related to the field of ultrasound imaging of medical devices within physiological structures and tissues.

BACKGROUND

The present application relates to hyperechogenic needles and methods for making and using the same, and more specifically, but not exclusively, concerns a needle having a hyperechogenic particulate material affixed to an outer surface of the needle to improve ultrasonic imaging properties of the needle.

Ultrasonic imaging techniques, such as 2D ultrasound, are widely used in modern medicine for multiple applications. In addition to imaging physiological structures and tissue such as nerves, organs, tumors, vessels, and the like, it is often desirable for a physician or technician to have an image of a medical device which has been inserted into the tissue or passageway of a patient. The types of devices that are surgically sterilized and inserted into patients are many. Typical examples include: needles, catheters and a variety of other medical products such as stents, dilators, pacing leads, introducers, angiography devices, angioplasty devices, pacemakers, inpatient appliances such as pumps and other devices. Ultrasound allows the practitioner to view anatomical structures in real time, which allows for greater precision in a given procedure.

One example of a technique that benefits from the use of 2D ultrasound is a needle biopsy technique, in which accurate placement of a needle tip in a specific target position is critical. Another example is peripheral nerve blockage, in which ultrasound imaging allows the clinician to view the nerve to be blocked in real time for accurate positioning of the needle tip. In using a 2D ultrasound apparatus to position a needle tip, the clinician is able to see below the skin, and thereby view the location of the needle tip relative to surrounding tissues. This renders greater precision in the procedure, and allows the clinician to advance the needle to the desired position relative to the tissues. In the case of peripheral nerve blockage, a local anesthetic can then be deposited near the nerve to be blocked.

Ultrasound energy comprises high frequency sound waves generated in the 2 to 15 MHz range. In common medical practice, a range of 5 to 12 MHz is employed for most applications, as this range provides optimal tissue resolution and penetration. The sound waves are commonly generated using a piezoelectric crystal. Piezoelectric crystals produce ultrasound energy when electrically stimulated, and also respond to reflected ultrasound energy. The ultrasound energy is pulsed and time locked. Ultrasound energy is typically reflected, and this reflected ultrasound energy is capable of amplification. Measuring reflected amplified energy enables the clinician to determine a range or distance to a tissue interface. Medical ultrasound techniques, such as 2D medical ultrasound, typically employ a piezoelectric effect reflective head, a computer, an electronic component, and a monitor to display the anatomy generated by the ultrasound integration of the tissue being examined.

An ultrasound head used in a typical 2D ultrasound technique includes a set of piezoelectric crystals in alignment, which crystals can be electronically switched on or off to respond to reflected ultrasound energy. The time delay between ultrasound emission and reflection can be used to construct a 2D picture of the tissue in alignment in the ultrasound plane generated. When the piezoelectric crystals are switched on and off electronically, a planar picture of the anatomy is created and displayed on the 2D ultrasound monitor. The 2D ultrasound apparatus allows tissue and anatomy to be visualized in both the axial and lateral direction. By controlling the switching order and timing of the individual piezoelectric crystals in the ultrasound head, the tissue can be scanned in a temporal fashion, thus creating a real time display of the tissue, and thus motion.

One major shortcoming of the use of a conventional needle in a 2D ultrasound technique is that the needle is often not easily visible in the plane of the 2D ultrasound beam. Maximum reflection of ultrasound energy occurs when the needle is at a 90° angle to the direction of the ultrasound waves in the 2D ultrasound plane. The signal degrades as this angle is reduced, to a point at which the needle becomes invisible in the 2D ultrasound plane. The ability to resolve a needle image on a 2D ultrasound monitor degrades as the needle moves from the 90° orientation to a lesser orientation, at which point it becomes invisible on a 2D monitor. This phenomenon is caused by specular reflectance, as the surface of the needle will only reflect ultrasound waves directly back to the ultrasound head. This reflectance is generally similar to the way that light is reflected from a mirror. The specular reflectance of the needle makes needle visualization with 2D ultrasound difficult. Commonly, the needle is invisible as it is advanced, greatly decreasing the utility of 2D ultrasound for determining needle tip placement. This effect makes use of 2D ultrasound in the placement of a needle problematic, since it is often ergonomically difficult to align it in the ultrasound head, define the tissue anatomy, and advance the needle in a 3D structure, while keeping the needle in view on the narrow 2D ultrasound plane.

To address concerns relating to decreasing the invasiveness of the procedures and improving patient outcomes, various approaches have been used to enhance ultrasonic imaging by modifying the reflective surface characteristics of needles and other devices. Optimal visualization of anatomical structures using 2D ultrasound reduces the likelihood of a practitioner misplacing the tip of a needle and reduces the number of attempts that would otherwise be necessary to accurately place the tip of a needle, decreasing the risk of inadvertent trauma to surrounding structures, such as, for example, accidental puncture of a blood vessel or accidental damage to a nerve.

A variety of approaches have been proposed to improve the echogenicity of needles and other medical devices; however, there is a need for provision of further improvement relating to the visualization of needles and other medical devices using two-dimensional ultrasound to provide accurate placement and monitoring of a surgical instrument such as a needle inserted into the body, which does not require a specific angle of orientation, and which is inexpensive to manufacture. The present application addresses this need.

SUMMARY

The foregoing need is addressed herein with a unique hyperechogenic needle having a structure and configuration that provides ease of manufacture and good imaging characteristics using two-dimensional ultrasonic imaging equipment. Other embodiments include unique methods, systems, devices, instrumentation, and apparatus involving a hyperechogenic needle.

In one aspect, the present application provides a needle effective for guided positioning in soft tissue of a patient with the aid of a real-time two-dimensional ultrasonic imaging apparatus. The needle includes (i) a rigid shaft having a longitudinal axis, a proximal end, a distal end, and an outer surface extending from the proximal end to the distal end, the distal end including a tip portion defining a point; (ii) a hyperechogenic particulate material affixed to the shaft along at least a portion of the outer surface, the hyperechogenic particulate material operable in response to a beam of ultrasound waves in a two-dimensional ultrasound plane to produce an image of the needle when the needle is in a position forming a non-90° angle between the longitudinal axis and the direction of the ultrasound waves in the two-dimensional ultrasound plane, thereby enhancing the ultrasonic imaging characteristics of the needle; and (iii) a polymeric coating positioned over at least a portion of the shaft and covering the hyperechogenic particulate material. In one embodiment, the polymeric coating has a lubricious external surface. In one embodiment, the hyperechogenic particulate material has a median average particle size of less than 18 microns. In another embodiment, the hyperechogenic particulate material has a median average particle size of less than 16 microns. In yet another embodiment, the hyperechogenic particulate material has a median average particle size of less than 12 microns. In various alternate embodiments, the median average particle size of the hyperechogenic particulate material is from about 1 to about 18 microns, from about 1 to about 16 microns, from about 1 to about 12 microns, from about 2 to about 18 microns, from about 2 to about 16 microns, from about 2 to about 12 microns, from about 3 to about 5 microns, or about 4 microns. In one embodiment, the hyperechogenic particulate material comprises a particulate talc material. In another embodiment, the hyperechogenic particulate material includes at least one of the following: a particulate talc material; a particulate calcium-containing material; a silicate, such as, for example, phyllosilicate, wollastonite, talc, montmorillonite, quartz, inosilicate or tectosilicate; a mineral including calcium, barium, aluminum or magnesium; or a carbonate, sulfate, oxide, hydroxide or phosphate of calcium, magnesium, barium or aluminum. The silicate can be, for example, wollastonite, talc, montmorillonite, quartz, or combinations thereof. The hyperechogenic material can be a ground mineral in its natural form, or can be a compound similar to a natural mineral, such as, for example, precipitated calcium carbonate. In another embodiment, the hyperechogenic particulate material includes at least one of graphite and silica. In addition, the particulate material can have a surface coating applied thereto, such as, for example, a stearic acid coating. In one embodiment, the shaft of the needle also includes an inner surface defining a lumen through the shaft, which can be used, for example, to deliver a drug or other material into a patient's body, or to draw fluid or tissue from the patient.

In one embodiment, at least a portion of the hyperechogenic particulate material is positioned between the shaft and the polymeric coating. In another embodiment, at least a portion of the hyperechogenic particulate material is dispersed in the polymeric coating. In an embodiment in which the hyperechogenic particulate material is dispersed in the polymeric coating, the hyperechogenic particulate material affixed to the shaft and the polymeric coating positioned over at least a portion of the shaft are combined into a single heterogeneous layer or coating, referred to herein as a hyperechogenic layer, over at least a portion of the shaft with the particulate material dispersed in the polymeric material. In this embodiment, the particulate material is preferably present at a concentration of from about 5 to about 25 weight percent, more preferably from about 10 to about 20 weight percent. In one embodiment, the hyperechogenic layer or the polymeric coating has a lubricious external surface. In another embodiment, the needle can also optionally include a friction lowering material, such as, for example, silicone affixed to the external surface of the hyperechogenic layer or the polymeric coating to provide a lubricious external surface. In an embodiment in which the needle is configured for use in blocking a nerve of a patient using simultaneous electrical nerve stimulation and two-dimensional ultrasound visualization of the nerve; the hyperechogenic layer or the polymeric coating composes an insulating layer covering at least a portion of the shaft. In such an embodiment, the shaft is electrically conductive, and the hyperechogenic layer or the polymeric layer covers substantially the entire shaft except not the tip portion.

In another aspect, the present application provides a system for guided placement of the tip of a needle that includes (i) a needle configured for insertion into soft tissue of a patient, the needle including (a) a rigid shaft having a longitudinal axis, a proximal end, a distal end, and an outer surface extending from the proximal end to the distal end, the distal end including a tip portion defining a point; (b) a hyperechogenic particulate material affixed to the shaft along at least a portion of the outer surface, the hyperechogenic particulate material operable in response to a beam of ultrasound waves in a two-dimensional ultrasound plane to produce an image of the needle when the needle is in a position forming a non-90° angle between the longitudinal axis and the direction of the ultrasound waves in the two-dimensional ultrasound plane, thereby enhancing the ultrasonic imaging characteristics of the needle; and (c) a polymeric coating positioned over at least a portion of the shaft and covering the hyperechogenic particulate material, the polymeric coating having a lubricious external surface; and (ii) a two-dimensional ultrasound apparatus capable of visualizing at least a portion of the needle in a segment of tissue of the patient. In one embodiment, the hyperechogenic particulate material comprises a particulate talc material. In another embodiment, the hyperechogenic particulate material comprises a member selected from the group consisting of a particulate talc material, a particulate calcium-containing material, a silicate, a mineral including calcium, barium, aluminum or magnesium and a carbonate, sulfate, oxide, hydroxide or phosphate of calcium, magnesium, barium or aluminum. The silicate can be, for example, wollastonite, talc, montmorillonite, quartz, or combinations thereof. The hyperechogenic material can be a ground mineral in its natural form, or can be a compound similar to a natural mineral, such as, for example, precipitated calcium carbonate. In another embodiment, the hyperechogenic particulate material includes at least one of graphite and silica. In another embodiment, the hyperechogenic particulate material has a median average particle size of less than 18 microns. In another embodiment, the hyperechogenic particulate material has a median average particle size of less than 16 microns. In yet another embodiment, the hyperechogenic particulate material has a median average particle size of less than 12 microns. In various alternate embodiments, the median average particle size of the hyperechogenic particulate material is from about 1 to about 18 microns, from about 1 to about 16 microns, from about 1 to about 12 microns, from about 2 to about 18 microns, from about 2 to about 16 microns, from about 2 to about 12 microns, from about 3 to about 5 microns, or about 4 microns. In addition, the particulate material can have a surface coating applied thereto, such as, for example, a stearic acid coating.

In an embodiment in which the needle is configured for use in blocking a nerve of a patient, the needle shaft is electrically conductive; the hyperechogenic layer or the polymeric coating is generally non-conductive; the hyperechogenic particulate material extends along at least a portion of a length of the shaft; and the system further includes a peripheral nerve stimulator capable of electrical connection with the shaft for transmitting an electrical pulse therethrough. The peripheral nerve stimulator preferably is capable of providing an adjustable current for eliciting a motor response.

In yet another aspect, the present application provides a method for positioning a needle in soft tissue of a patient with the aid of a real-time two-dimensional ultrasonic imaging apparatus. The method includes: (i) providing a needle that includes a rigid shaft having a longitudinal axis, a proximal end, a distal end, and an outer surface extending from the proximal end to the distal end, the distal end including a tip portion defining a point, and a hyperechogenic particulate material affixed to the shaft along at least a portion of the outer surface, the hyperechogenic particulate material being operable in response to a beam of ultrasound waves in a two-dimensional ultrasound plane to produce an image of the needle when the needle is in a position forming a non-90° angle between the longitudinal axis and the direction of the ultrasound waves in the two-dimensional ultrasound plane, thereby enhancing the ultrasonic imaging characteristics of the needle; (ii) inserting the needle into soft tissue of a patient; (iii) visualizing the needle with a two-dimensional ultrasound imaging apparatus; and (iv) manipulating the needle tip to a desired location in the tissue under real-time two-dimensional ultrasound imaging. In one embodiment, the hyperechogenic particulate material comprises a particulate talc material. In another embodiment, the hyperechogenic particulate material includes at least one of the following: a particulate talc material, a particulate calcium-containing material, a silicate, a mineral including calcium, barium, aluminum or magnesium and a carbonate, sulfate, oxide, hydroxide or phosphate of calcium, magnesium, barium or aluminum. The silicate can be, for example, wollastonite, talc, montmorillonite, quartz, or combinations thereof. The hyperechogenic material can be a ground mineral in its natural form, or can be a compound similar to a natural mineral, such as, for example, precipitated calcium carbonate. In another embodiment, the hyperechogenic particulate material includes at least one of graphite and silica. In another embodiment, the hyperechogenic particulate material has a median average particle size of less than 18 microns. In another embodiment, the hyperechogenic particulate material has a median average particle size of less than 16 microns. In yet another embodiment, the hyperechogenic particulate material has a median average particle size of less than 12 microns. In various alternate embodiments, the median average particle size of the hyperechogenic particulate material is from about 1 to about 18 microns, from about 1 to about 16 microns, from about 1 to about 12 microns, from about 2 to about 18 microns, from about 2 to about 16 microns, from about 2 to about 12 microns, from about 3 to about 5 microns, or about 4 microns. In addition, the particulate material can have a surface coating applied thereto, such as, for example, a stearic acid coating.

In still another aspect of the present application, there is provided a method for blocking a nerve of a patient that includes: (i) providing a hyperechogenic stimulating block needle, the needle comprising an electrically conductive rigid shaft having a longitudinal axis, a proximal end, a distal end, and an outer surface extending from the proximal end to the distal end, the distal end including a tip portion defining a point; a hyperechogenic particulate material affixed to the shaft along at least a portion of the outer surface, the hyperechogenic particulate material operable in response to a beam of ultrasound waves in a two-dimensional ultrasound plane to produce an image of the needle when the needle is in a position forming a non-90° angle between the longitudinal axis and the direction of the ultrasound waves in the two-dimensional ultrasound plane, thereby enhancing the ultrasonic imaging characteristics of the needle; and a polymeric coating positioned over at least a portion of the shaft and covering the hyperechogenic particulate material, the polymeric coating having a lubricious external surface; (ii) inserting the tip portion into a patient; (iii) aligning the tip portion in proximity with the nerve by visualization with two-dimensional ultrasound imaging and by electrical nerve stimulation; and (iv) injecting a local anesthetic drug through the lumen defined by the shaft into the patient. In one embodiment, the hyperechogenic particulate material comprises a particulate talc material. In another embodiment, the hyperechogenic particulate material comprises a member selected from the group consisting of a particulate talc material, a particulate calcium-containing material, a silicate, a mineral including calcium, barium, aluminum or magnesium and a carbonate, sulfate, oxide, hydroxide or phosphate of calcium, magnesium, barium or aluminum. The silicate can be, for example, wollastonite, talc, montmorillonite, quartz, or combinations thereof. The hyperechogenic material can be a ground mineral in its natural form, or can be a compound similar to a natural mineral, such as, for example, precipitated calcium carbonate. In another embodiment, the hyperechogenic particulate material includes at least one of graphite and silica. In another embodiment, the hyperechogenic particulate material has a median average particle size of less than 18 microns. In another embodiment, the hyperechogenic particulate material has a median average particle size of less than 16 microns. In yet another embodiment, the hyperechogenic particulate material has a median average particle size of less than 12 microns. In various alternate embodiments, the median average particle size of the hyperechogenic particulate material is from about 1 to about 18 microns, from about 1 to about 16 microns, from about 1 to about 12 microns, from about 2 to about 18 microns, from about 2 to about 16 microns, from about 2 to about 12 microns, from about 3 to about 5 microns, or about 4 microns. In addition, the particulate material can have a surface coating applied thereto, such as, for example, a stearic acid coating.

Yet another aspect of the present application is a method for making a needle for guided positioning in soft tissue of a patient with the aid of a real-time two-dimensional ultrasonic imaging apparatus. The method includes: (i) providing a rigid shaft having a longitudinal axis and an outer surface; (ii) applying to at least a portion of the outer surface a hyperechogenic particulate material; and (iii) applying over at least a portion of the shaft a polymeric coating having a lubricious external surface. In an embodiment in which the needle includes a hyperechogenic layer having the hyperechogenic particulate material dispersed in a polymeric material, the applying the hyperechogenic particulate material and applying the polymeric coating of the method can be achieved by applying a mixture of the particulate material the polymeric material to the outer surface. This can be accomplished, for example, using a powder coating technique.

In one embodiment, the shaft has sufficient length to produce multiple needles therefrom, and the method further comprises cutting the shaft into desired lengths to provide a plurality of needles, and forming a point on one end of each needle. The hyperechogenic particulate material when affixed to the outer surface of a needle, is operable in response to a beam of ultrasound waves in a two-dimensional ultrasound plane to produce an image of the needle when the needle is in a position forming a non-90° angle between the longitudinal axis and the direction of the ultrasound waves in the two-dimensional ultrasound plane, thereby enhancing the ultrasonic imaging characteristics of the needle. In one embodiment, the hyperechogenic particulate material comprises a particulate talc material. In another embodiment, the hyperechogenic particulate material comprises a member selected from the group consisting of a particulate talc material, a particulate calcium-containing material, a silicate, a mineral including calcium, barium, aluminum or magnesium and a carbonate, sulfate, oxide, hydroxide or phosphate of calcium, magnesium, barium or aluminum. The silicate can be, for example, wollastonite, talc, montmorillonite, quartz, or combinations thereof. The hyperechogenic material can be a ground mineral in its natural form, or can be a compound similar to a natural mineral, such as, for example, precipitated calcium carbonate. In another embodiment, the hyperechogenic particulate material includes at least one of graphite and silica. In addition, the particulate material can have a surface coating applied thereto, such as, for example, a stearic acid coating.

Further embodiments, forms, features, aspects and benefits of the present application shall become apparent from the detailed description and figures provided herewith.

BRIEF DESCRIPTION OF THE DRAWINGS

FIG. 6 is a longitudinal cross section elevation view of a hyperechogenic nerve block needle embodiment.

DETAILED DESCRIPTION OF SELECTED EMBODIMENTS

Figure 1:
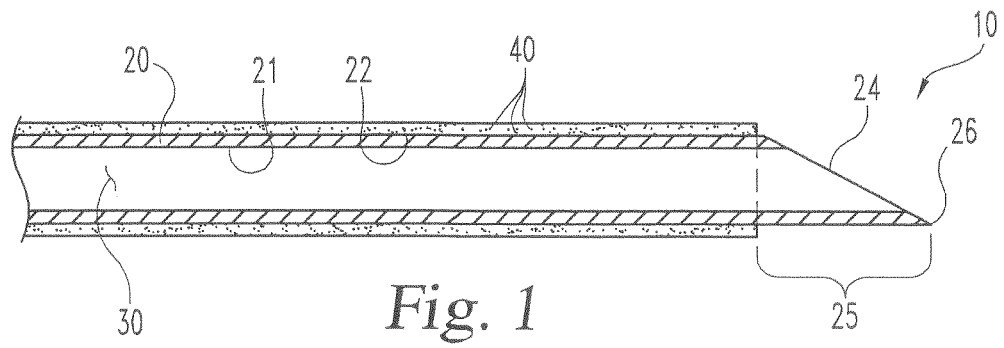
FIG. 1 is a longitudinal cross section elevation view of a hyperechogenic needle embodiment.

For the purpose of promoting an understanding of the principles of the invention, reference will now be made to the embodiments illustrated in the drawings and specific language will be used to describe the same. The following description is intended to convey a thorough understanding of the present invention by providing a number of specific embodiments and details involving hyperechogenic needles, methods of their manufacture, and methods of their use. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Hyperechogenic needles described herein have good echogenicity, and thus good ultrasound imaging characteristics (i.e., show up under 2D ultrasound as a very bright echo) as a result of having at least one hyperechogenic particulate material affixed to at least a portion of the needle's shaft, which provides a needle having good ultrasound visualization properties. As used herein, the term "echogenicity" refers to the characteristic of reflecting an ultrasound wave back to a transducer of an ultrasound imaging apparatus; the term "hyperechogenic" refers to a device or material that exhibits enhanced echogenicity compared to another device or material. The phrase "hyperechogenic particulate material" refers to a material that can be provided in a powder, a slurry or other particulate form, and that, when affixed to at least a portion of the shaft of a needle, is effective to increase the two-dimensional ultrasonic imaging visualization properties of the needle after insertion thereof into soft tissue of a patient. While it is not intended that the present invention be limited by any theory of operation, it is believed that surface properties of the particles and/or the physical properties of the particulate material causes ultrasound waves that contact the material to travel in multiple directions and in a more random fashion than with conventional needles, and that the increase in scatter and/or reflection of the ultrasound waves enhances the temporal visualization of the hyperechogenic needle path and tip during 2D ultrasound examination. As a result, the image of a hyperechogenic needle as described herein that is produced by ultrasonic imaging equipment is enhanced compared to a needle without the hyperechogenic particulate material.

More particularly, the presence of the hyperechogenic particulate material improves the axial, lateral and temporal resolution of the needle under 2D ultrasound. In practice, the particulate material enhances the visibility of the needle under 2D ultrasound, regardless of the needle orientation to the ultrasound head. The needle will appear on the 2D ultrasound monitor in real time, and the needle position, needle path tip, and interaction with the tissue will be visible in real time. As a result, because the needle is more highly visible on a 2D ultrasound monitor, the needle may be more safely and accurately advanced toward a target location using the 2D ultrasound monitor.

In the present specification, the terms "proximal" and "distal" are used to describe the opposing axial ends of a needle, as well as the axial ends of various components thereof. The term "proximal" is used in its conventional sense to refer to a direction toward the end of a needle (or component thereof) that is closest to the operator during use of the needle. The term "distal" is used in its conventional sense to refer to a direction toward the end of a needle (or component thereof) that is initially inserted into the patient, i.e., that is furthest from the operator, or closest to the patient, during use of the needle.

With reference to FIG. 1, which shows a distal end portion of needle 10, needle 10 includes rigid shaft 20 having inner surface 21 defining lumen 30 therethrough. Shaft 20 also has outer surface 22, proximal end (not shown in this view) and distal end 24. Distal end 24 defines distal tip portion 25. Distal tip portion 25 of shaft 20 includes a sharp tissue-penetrating point 26, which has sufficient sharpness to enable the needle to puncture the patient's skin, and advance more easily through tissue, while minimizing tissue trauma. In one embodiment, point 26 is formed as an arcuate or beveled configuration of tip portion 25, and more preferably, a short bevel tip. Although the short bevel tip is not restricted to a particular bevel angle, in a preferred embodiment, the bevel angle is about 45°. Those skilled in the art will appreciate that beveled tips at angles other than 45° (such as less than 45°) may be preferred in certain circumstances, and such tips are also within the scope of the invention. Typically, short bevel tips require more force during insertion than long bevels. However, this additional exertion of force enables the clinician to better "feel" the texture of the tissue as the tip is advanced, thereby helping to identify the tip location. Those skilled in the art are very familiar with various needle tips, and are suitably equipped to select a satisfactory tip for a particular application in view of the teachings of the present invention. In another embodiment (not shown), the needle is of a type that includes a side port near the distal end of the needle. For example, a needle having a side port may be of the type commonly known as a Whitacre needle, examples of which are well known and commercially available. In addition, the distal tip of the needle can have a "pencil tip" configuration as an alternative to a beveled tip as shown in the figures. While multiple examples of needle configurations are described herein, it is not intended that the present invention be limited to these configurations, it being understood that various features and elements described herein can be applied to needles having a wide variety of configurations. Shaft 20 can be composed of any suitable rigid material, and in one preferred embodiment is made of a metal or metal alloy, such as surgical grade steel.

Hyperechogenic particulate material 40 is affixed to shaft 20 along at least a portion of outer surface 22. Hyperechogenic particulate material 40 is operable in response to an ultrasonic beam to produce an image of the needle, thereby enhancing the ultrasonic imaging characteristics of the needle. In certain preferred embodiments, hyperechogenic particulate material 40 has one or more of the following characteristics: it is of a type that can be incorporated into and dispersed in a polymer coating (preferably being capable of binding well with the polymer), it is one that is capable of withstanding mechanical stress and aging in the environments in which is shipped, stored and/or used, it is biocompatible, it is stable in the environments in which it is made, shipped, stored, sterilized and/or used, it does not degrade the polymer surface in which it is dispersed under any of the conditions mentioned above or any other conditions in which it is placed in ordinary handling or use, and it is relatively inexpensive and abundant. Hyperechogenic particulate material 40 can be comprised of a variety of materials or combinations of materials that enhance the clarity of an image produced by a 2D ultrasound apparatus. For example, the hyperechogenic particulate material in one embodiment is comprised of a particulate talc material, such as, for example a particulate platy talc material. Alternatively, in some embodiments described herein, the hyperechogenic particulate material is comprised of a calcium-containing material, such as, for example, particulate calcium carbonate, which in alternative embodiments can be ground calcium carbonate ("GCC") or precipitated calcium carbonate ("PCC"), calcium phosphate or hydroxyapatite. In one embodiment, the hyperechogenic particulate material is a mineral including calcium, barium, aluminum or magnesium, such as, for example, calcite or aragonite (which include calcium carbonate), dolomite (which includes magnesium carbonate and calcium carbonate), barite (which includes barium sulfate) and hydroxyapatite. In another embodiment, the hyperechogenic particulate material is a silicate (including phyllosilicate, wollastonite, talc, montmorillonite, quartz, inosilicate or tectosilicate) or a carbonate, sulfate, oxide, hydroxide or phosphate of calcium, magnesium, barium or aluminum. In another embodiment, the hyperechogenic particulate material includes at least one of graphite and silica. It is not intended, however, that the identification of certain materials above be considered limiting, but rather identify representative examples of suitable hyperechogenic particulate materials.

Talc has been found to exhibit particularly strong echogenic characteristics when used as the hyperechogenic particulate material 40 as described herein. While not intended to be limited by any particular theory, it is known that talc tends to form in plates in nature and has a high aspect ratio (length divided by thickness). It is believed that talc's platyness when dispersed in a polymer or a resin may account for some of talc's strong echogenic characteristics, perhaps by producing a plurality of acoustical irregularities, along with increased ultrasound scattering. In addition, talc is oilophilic, which allows talc to be loaded at a relatively high weigh percent compared to other particulate materials, thus allowing a relatively high amount of platy microcrystalline talc particles to be included in a polymer or resin used to affix the particles to a needle surface. Additional features of talc that make it an excellent material for use as described herein include its relative abundance, it is relatively inexpensive, it has been extensively studied and used in multiple applications and in multiple fields, including in plastics technologies and the healthcare field, it is electrically nonconductive, which enables it to be used in outer insulating layers of nerve stimulator needles and other electrical devices, and it is chemically inert.

In one embodiment, the talc material used as a hyperechogenic particulate material as described herein has a median particle size range of from about 2 to about 16 microns. As will be appreciated by a person of ordinary skill in the art a talc material having a particle size distribution with a median particle size within the recited range can include particles that are not within the range. In another embodiment, the talc material has a median particle size range of less than 2 microns.

Hyperechogenic particulate material 40 can be affixed to outer surface 22 of shaft 20 in any manner as would occur to a person of ordinary skill in the art, provided that the manner of affixation is effective to minimize the separation of particles from the shaft during use, and provided that, if any materials used to affix the particulate material, such as, for example, an adhesive, a resin, a polymer or the like, is exposed directly to living tissues during normal use of the needle, such material is biocompatible or otherwise suitable for contact with living tissues without having a detrimental effect on the tissue. In one embodiment, particulate material 40 is adhered to outer surface 22 of a shaft 20 using a medical grade adhesive. In another embodiment, particulate material 40 is adhered to outer surface 22 of shaft 20 using a biocompatible resin. In yet another embodiment, which is described in greater detail hereinbelow, particulate material 40 is adhered to outer surface 22 of shaft 20 by affixing a polymeric coating to surface 22 in which coating the particulate material 40 is dispersed. In one embodiment, the particulate material is a treated particulate material. As used herein, the term "treated particulate material" is used to refer to a particulate material to which a surface coating, such as, for example, a stearic acid coating has been applied. Such a surface coating has been observed to aid in dispersion of the particulate materials in the adhesive or resin material.

Particulate material 40 may also be composed of more than one type of particle. For example, in one embodiment, particulate material 40 comprises a mixture of a particulate talc and a particulate coated, ground calcium carbonate. The term "coated" means that the ground calcium carbonate includes a surface coating as described above, such as, for example, a coating of stearic acid, and is therefore a treated particulate material. In another embodiment, particulate material 40 comprises a mixture of particulate talc and a particulate uncoated ground calcium carbonate. In yet another embodiment, particulate material 40 comprises a mixture of particulate talc, a particulate coated ground calcium carbonate and a particulate wollastonite material. In one embodiment, particulate material 40 includes from zero to about 70 percent talc by weight and from zero to about 70 percent calcium carbonate by weight. In one embodiment, the particulate talc has a median particle size of from about 11 to about 16 microns and the ground calcium carbonate has a median particle size of from about 3 to about 4 microns. In another embodiment, the particulate talc has a median particle size of from about 2 to about 16 microns and the ground calcium carbonate has a median particle size of from about 1 to about 6 microns. Hyperechogenic particulate material 40 is preferably present in an amount sufficient to coat outer surface 22 of shaft 20 to a degree whereby an ultrasonic image produced by particulate material 40 is uniform on an ultrasound apparatus display.

While the embodiments depicted in the Figures show particulate material 40 as being present in a continuous layer surrounding shaft 20 from a point adjacent distal tip portion 25 toward the proximal end (not shown) of needle shaft 20, it is to be understood that an embodiment with such a continuous layer shown only as a representative example. It is not intended that the present application be limited to such continuous configurations, it being understood that a variety of other configurations can be employed. For example, in another embodiment, hyperechogenic particulate material 40 is not continuous along the length of the needle. Rather, the hyperechogenic particulate material may be discontinuous along the needle axis or may otherwise vary along the shaft of the needle, and the length of the needle may include discrete portions having, and not having, hyperechogenic particulate material. For example, in one embodiment particulate material 40 surrounds shaft 20 from a proximal end of shaft 20 all the way to distal tip 25. In another embodiment (not shown), particulate material 40 is formed into a distinctive pattern just proximal to tip portion 25 to clearly communicate to a clinician the position of tissue-penetrating point 26 by its proximity to the distinctive pattern. In yet another embodiment (not shown) particulate material 40 surrounds shaft 20 only adjacent tip portion 25, but does not extend proximally along shaft 20 to its proximal end. In yet another embodiment, wherein particulate material 40 is dispersed in a polymeric material such as in hyperechogenic layer 260 depicted in FIG. 5, portions of hyperechogenic layer 260 can be removed to provide distinctive patterns on the surface of shaft 20. In one manner of providing distinctive patterns on shaft 20, laser etching is used to remove portions of hyperechogenic layer 260. Alternative methods of removing portions of hyperechogenic layer 260 can also be used in other embodiments. Such alternative arrangements as would occur to a person of ordinary skill in the art are effective to provide additional contrast along the needle surface, thereby allowing the clinician to delineate position, path, and length of the needle using 2D ultrasound. Similarly, the hyperechogenic particulate material need not be structured to provide only a single type of echogenic signal. Rather, the hyperechogenic particulate material may be positioned at more than one location along the shaft of the needle, and may have differing patterns or sizes to provide different types of echogenic signals along the needle axis, thereby providing additional contrast and/or visibility along the needle surface to provide additional information to a clinician using the needle.

Figure 2A:
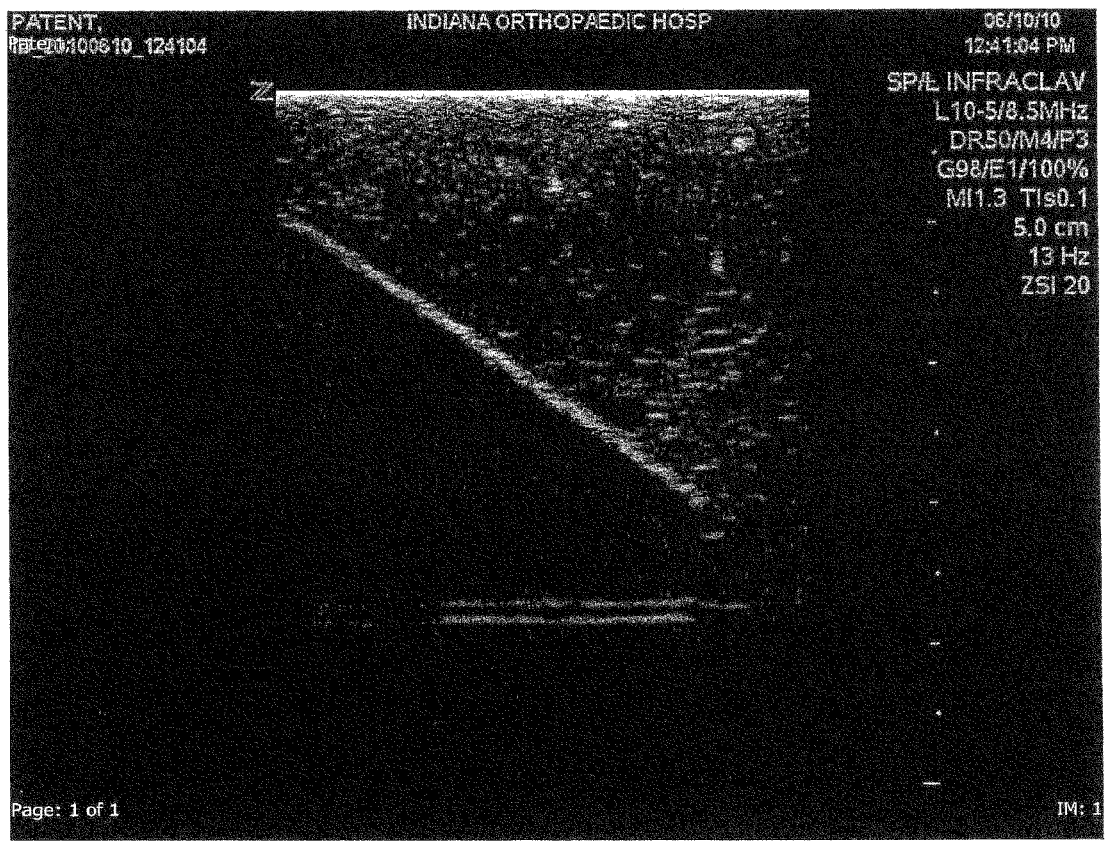
FIGS. 2A-2H are digital images of 2D ultrasound displays showing hyperechogenic needle embodiments.
Figure 2B:
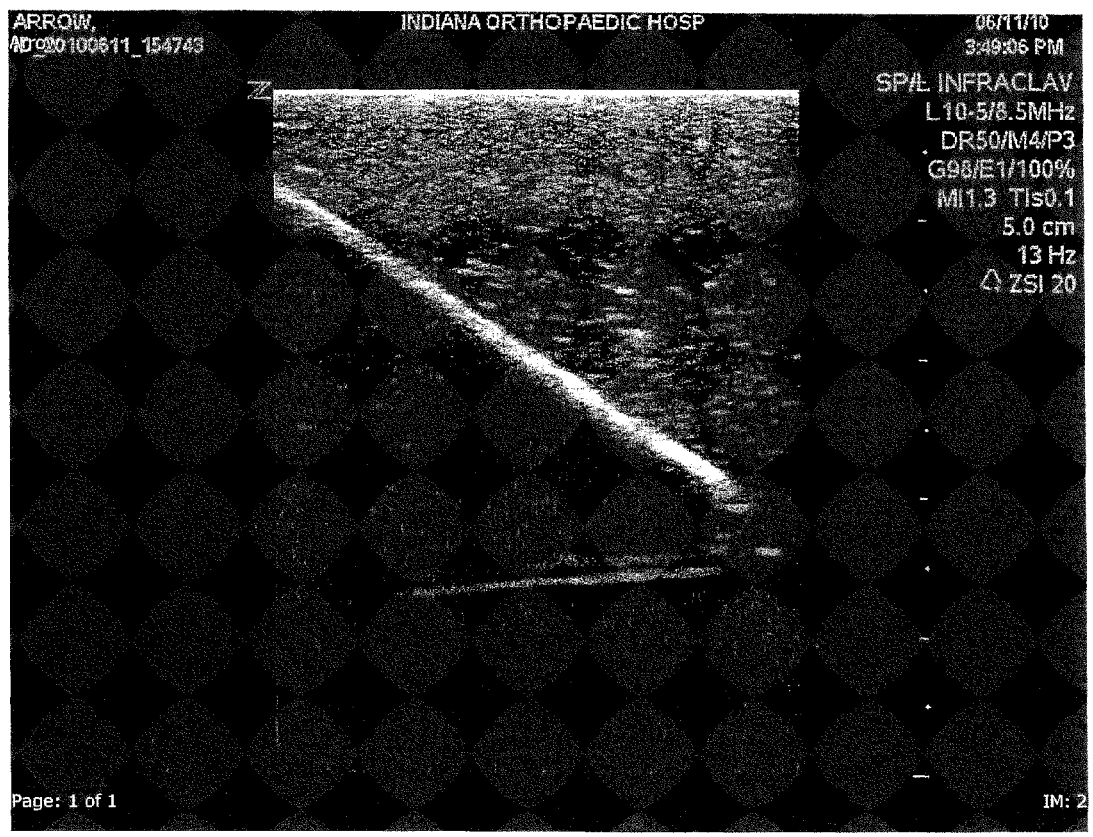
Figure 2C:
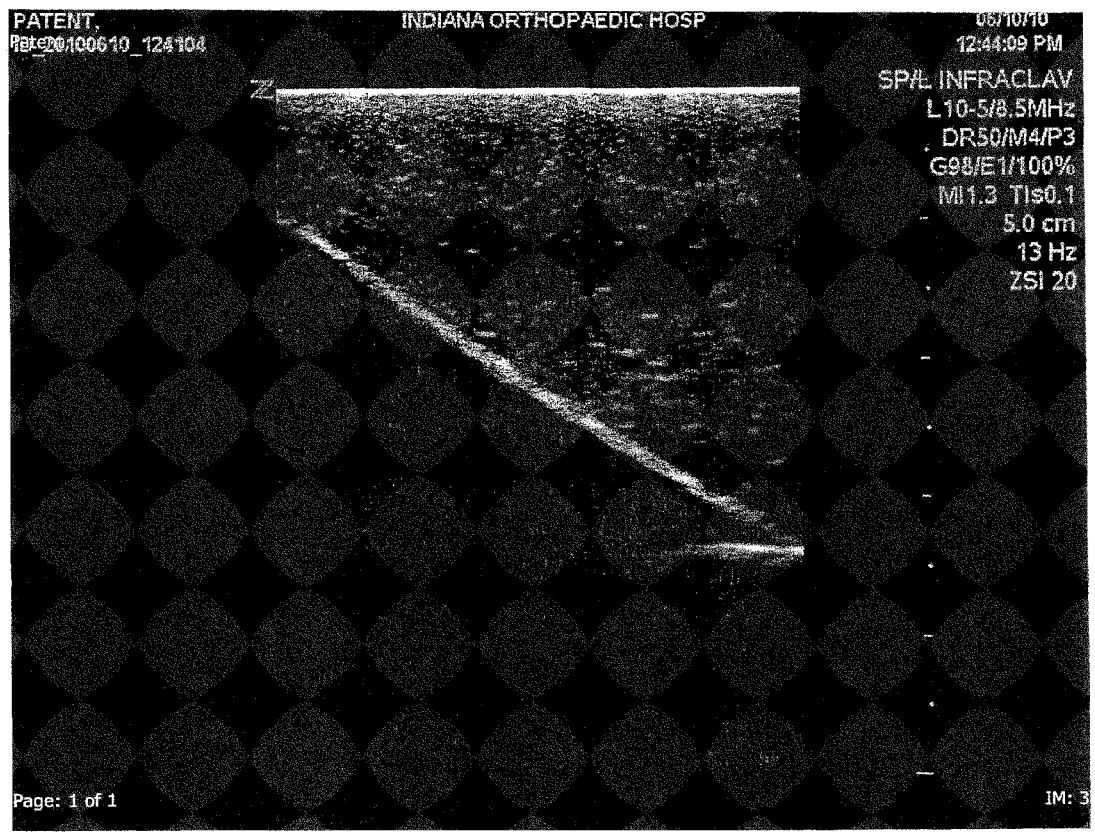
Figure 2D:
Figure 2E:
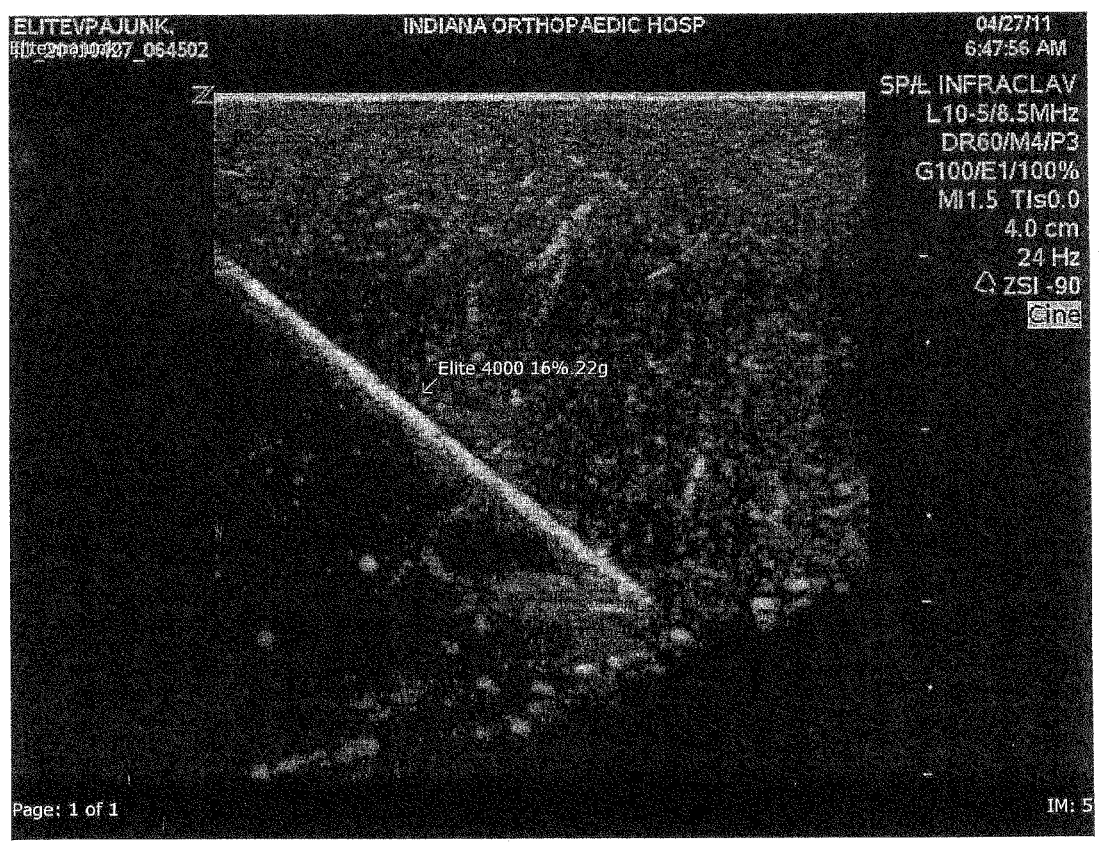
Figure 2F:
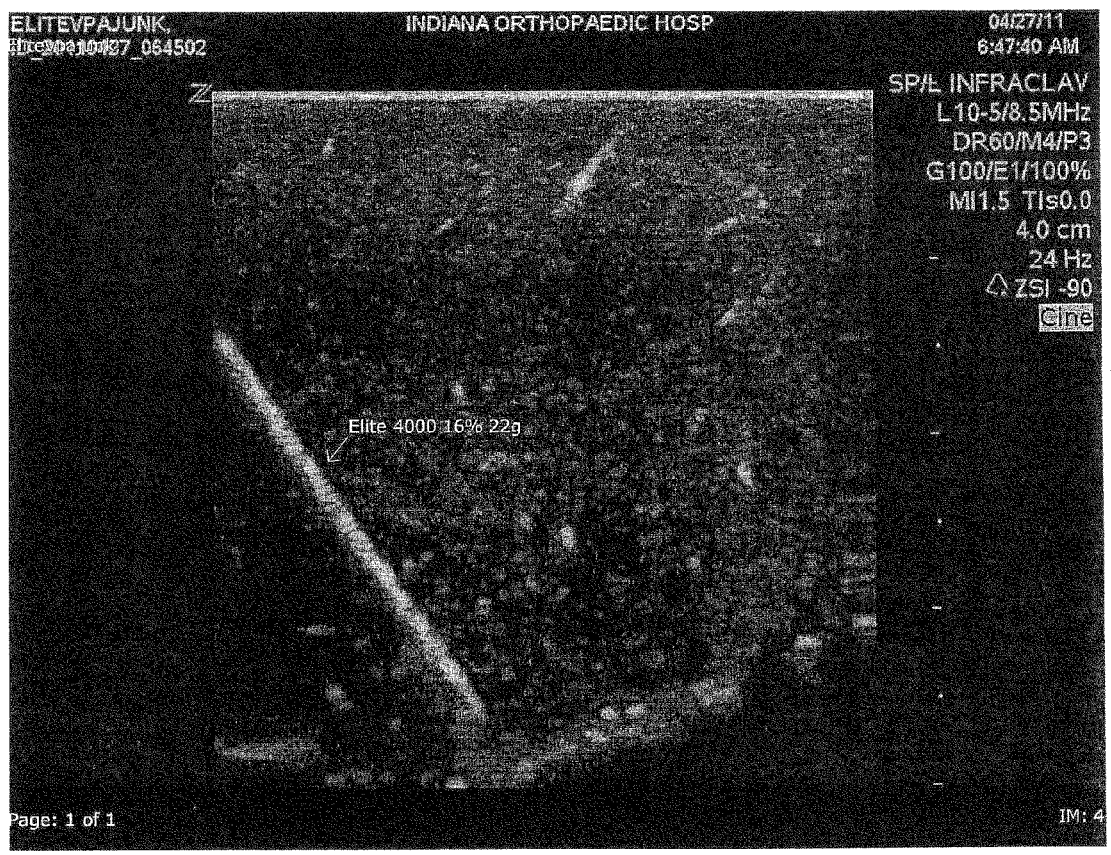
Figure 2G:
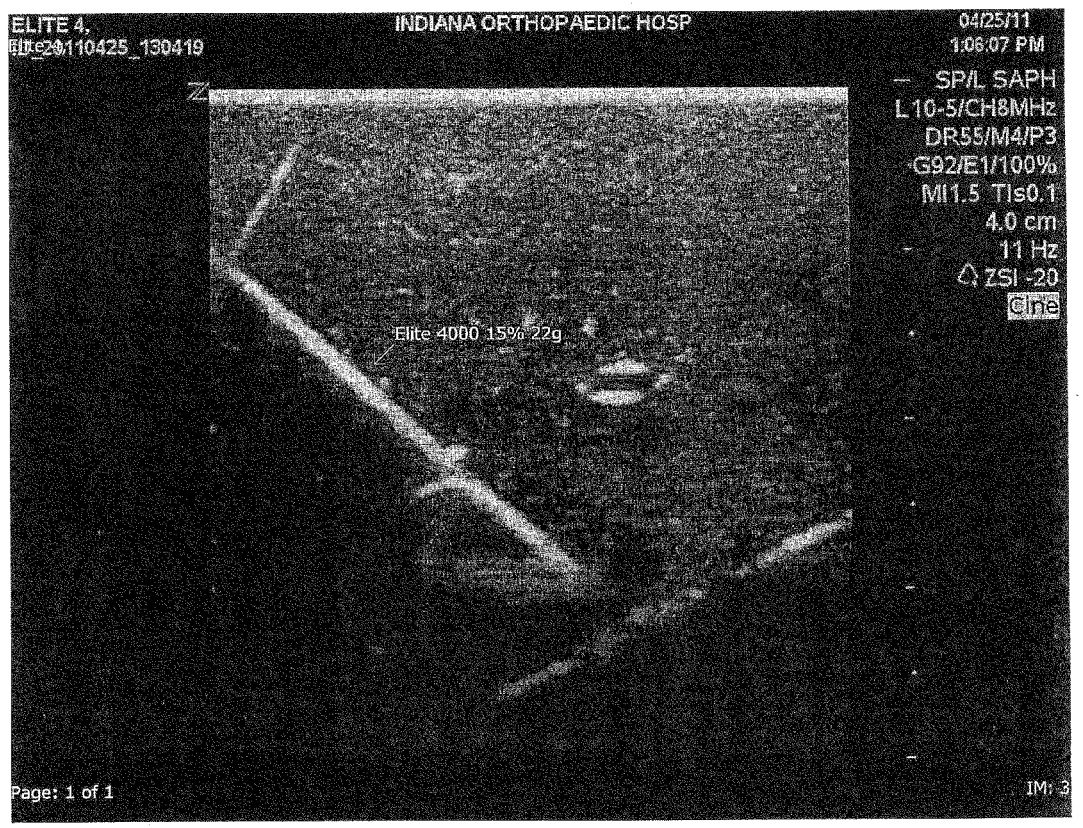
Figure 2H:
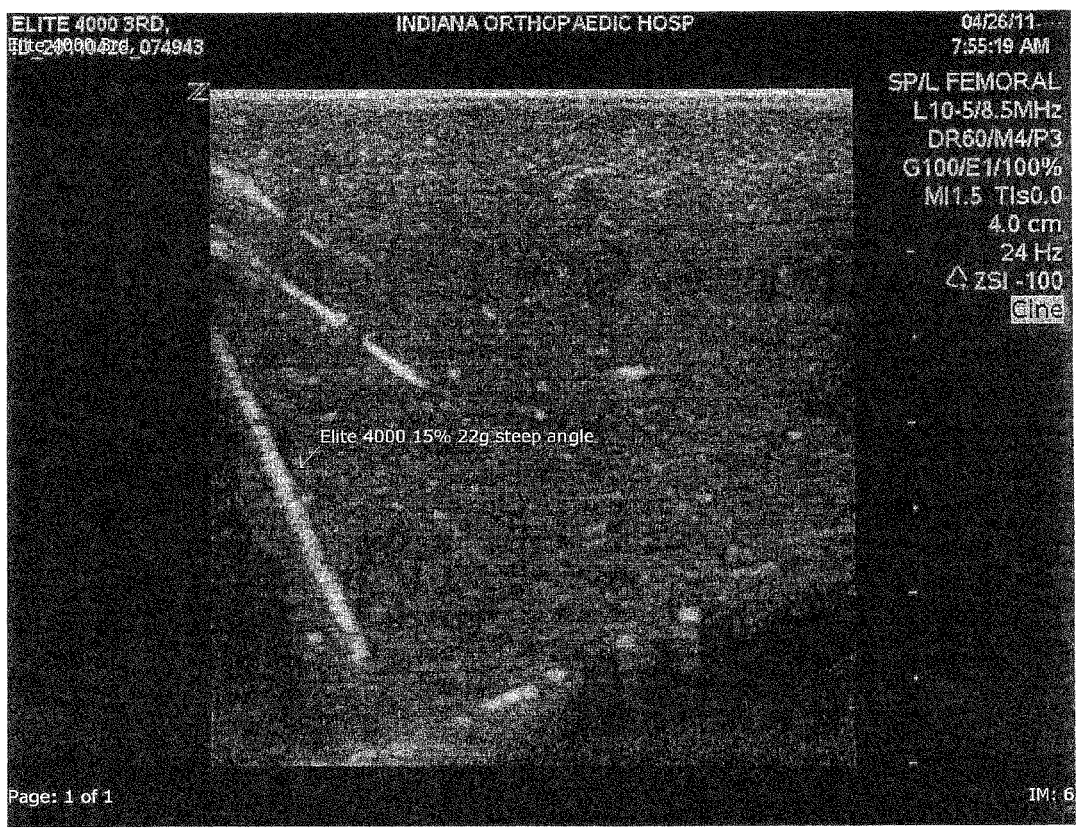
Figure 3A:
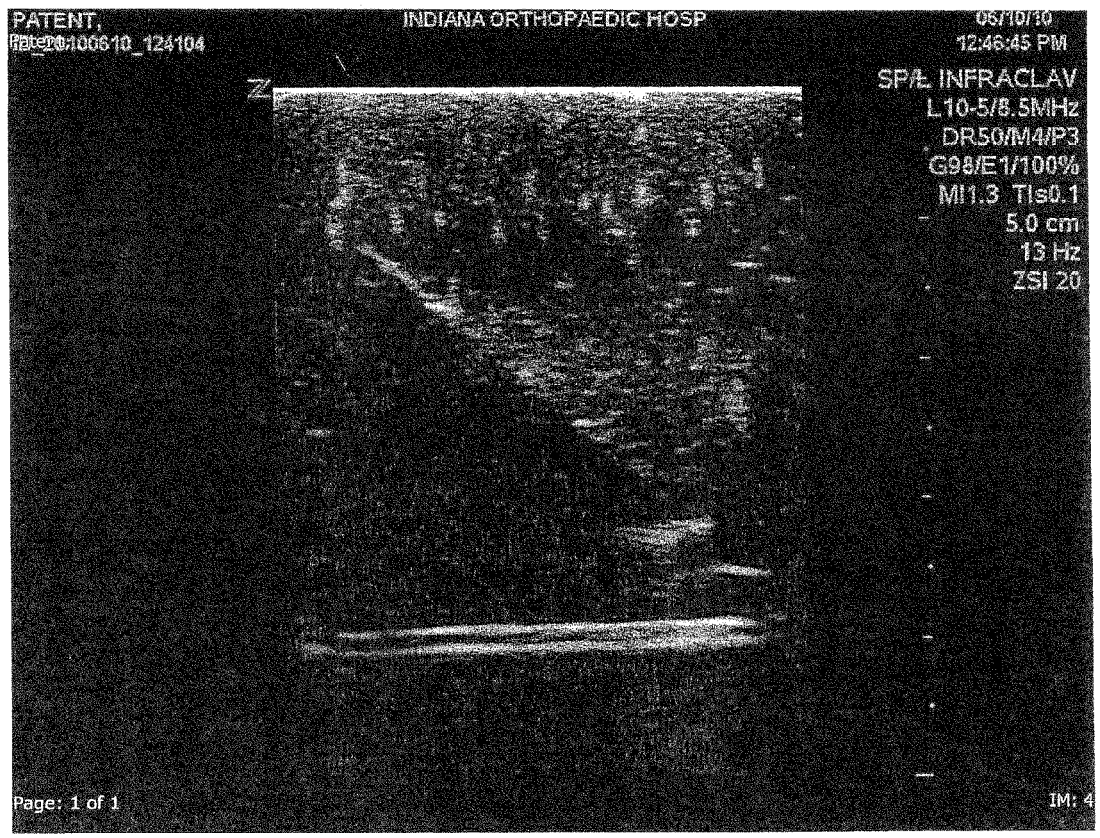
FIGS. 3A-3F are digital images of 2D ultrasound displays showing standard prior art needles, or a commercially available echogenic needle, that do not include a hyperechogenic particulate material as described herein.
Figure 3B:
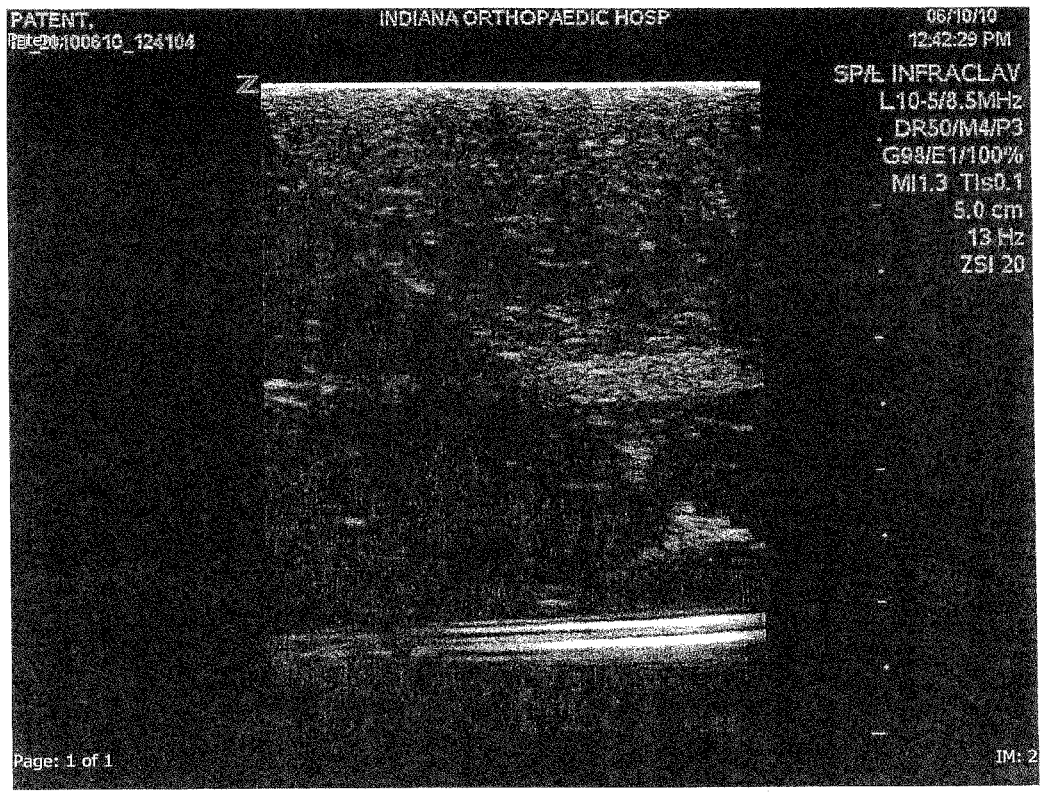
Figure 3C:
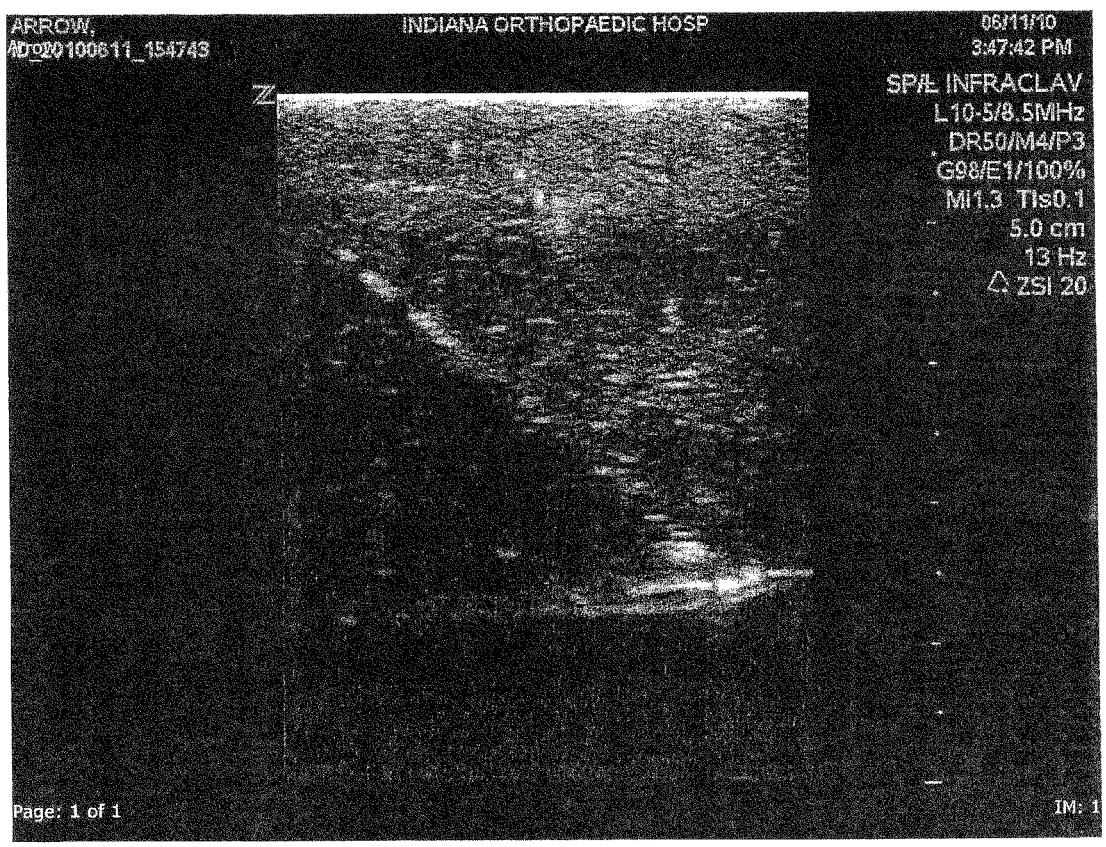
Figure 3D:
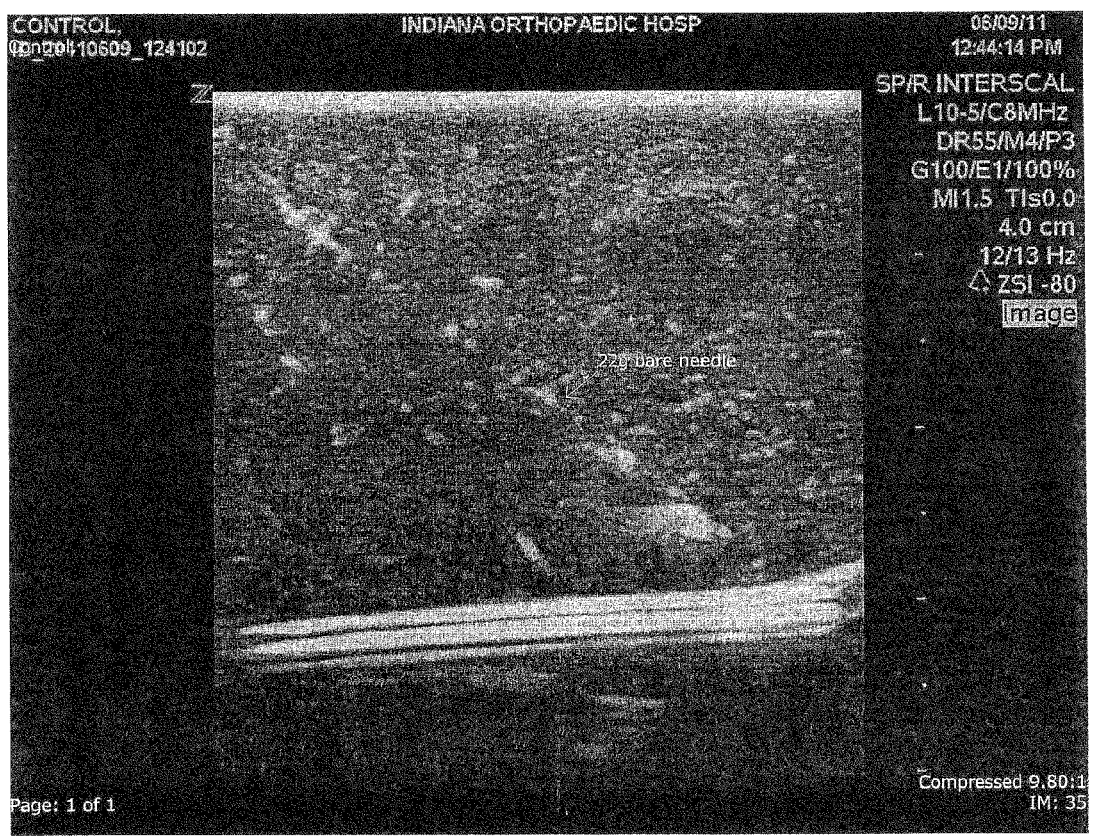
Figure 3E:
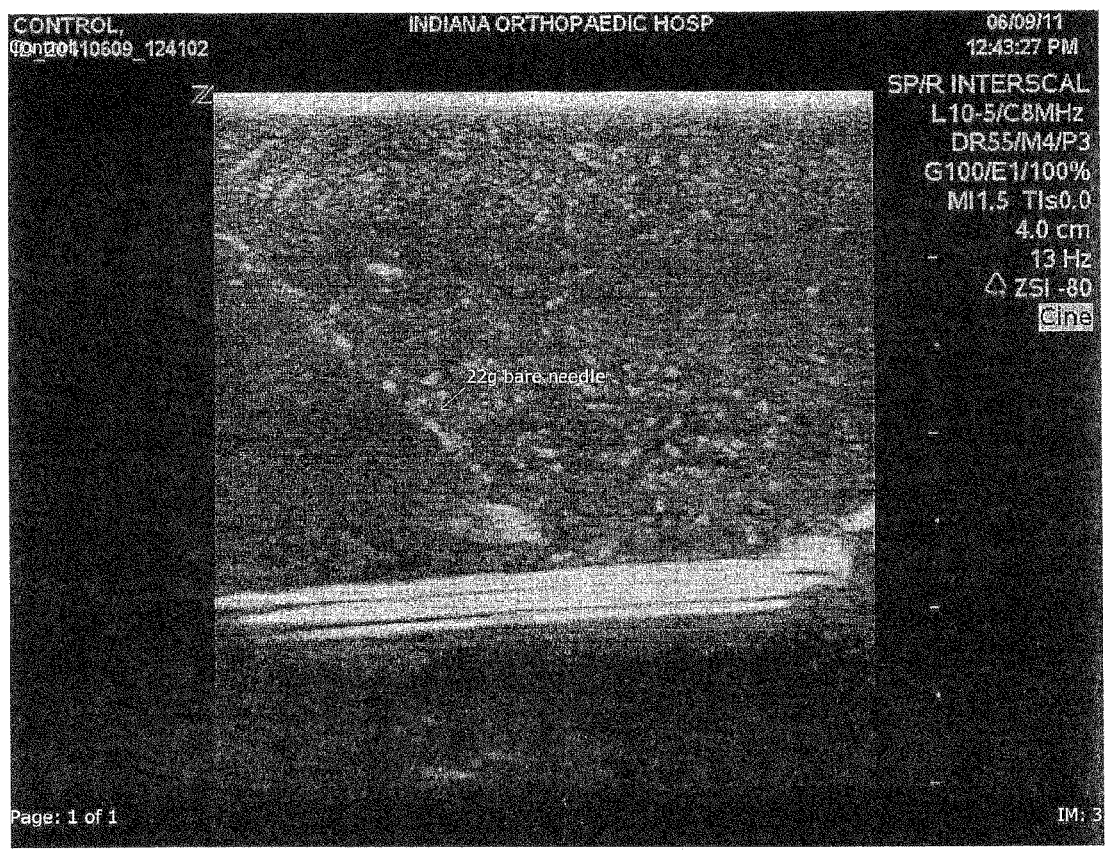
Figure 3F:
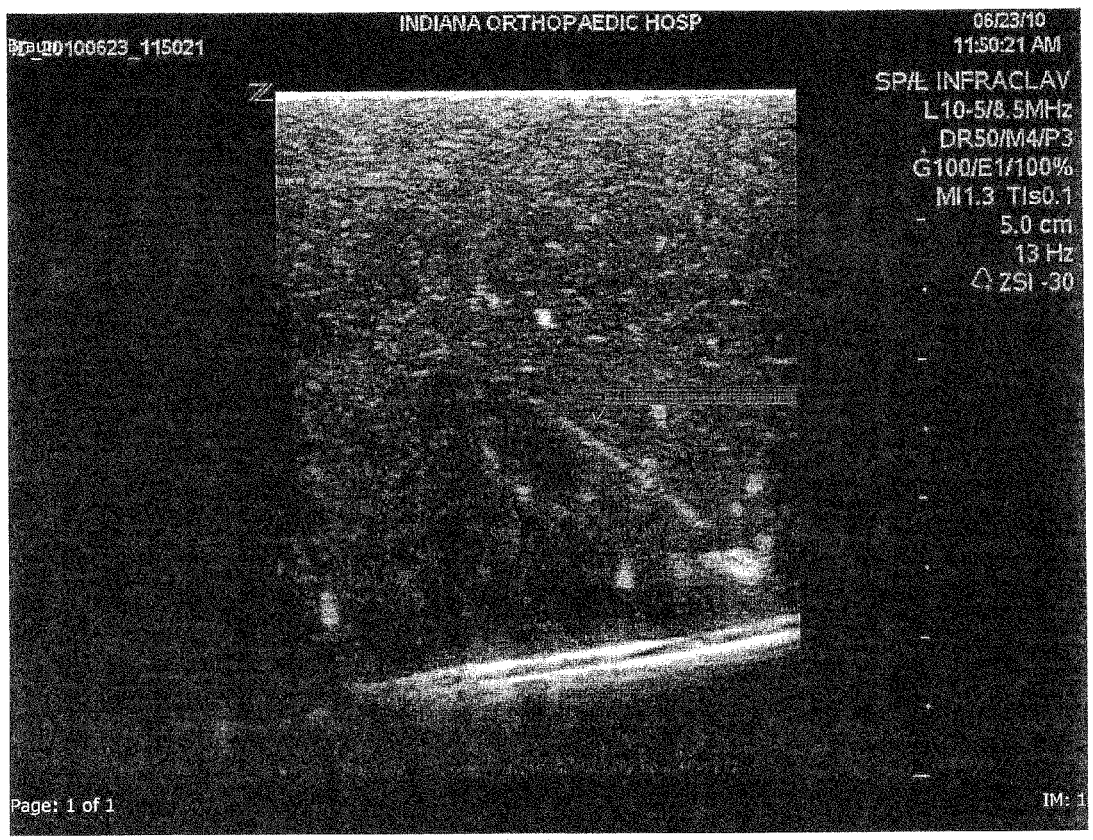

FIGS. 2A-2D depict four print-outs from the display of a 2D ultrasound monitor (Zonare™ ultrasound system) of a needle in a Blue Phantom™ ultrasound training model tissue block, the needle having particulate material 40 affixed to outer surface 22 of shaft 20, particulate material 40 including a mixture of a talc particulate material and a calcium carbonate particulate material. FIGS. 2E-2H depict four print-outs from the display of a 2D ultrasound monitor (Zonare™ ultrasound system) of a needle in Blue Phantom™ ultrasound training model tissue block, the needle having particulate material dispersed in a polymeric material to provide a hyperechogenic layer in the form of hyperechogenic layer 260 as described hereinbelow, with the polymeric material operating as a matrix or scaffold in which particulate material 40 is embedded. Particulate material 40 in the embodiment shown in FIGS. 2E-2H is a talc particulate material having an average median size of 3.8 microns dispersed in PET at a concentration of 15 or 16 weight percent, respectively (as shown in the Figures). Particulate material 40 renders the needle visible as it moves from a 90° orientation (e.g., perpendicular) to the direction of the ultrasound waves to an orientation that approaches an alignment with the ultrasound waves. The needle image on a 2D ultrasound monitor is thus visible with greater resolution than may be achieved with a needle without hyperechogenic particulate material, both at a 90° angle, and at lesser angles. In FIG. 2D, the needle image is visible after the needle has rotated 35° from the perpendicular orientation described. Similarly, in FIG. 2H, the needle image is visible after the needle has rotated to a steeper angle from the perpendicular orientation. This reflection is different than specular reflectance, since it results from the scattering of the ultrasound waves by the hyperechogenic particulate material 40. In this case, wave scattering occurs toward the 2D ultrasound head to make the needle image visible at various angles in the 2D ultrasound plane For the sake of comparison, FIGS. 3A-3E depict five print-outs from the display of the same 2D ultrasound monitor of a bare needle (i.e., without particulate material 40) and FIG. 3F depicts a print-out from the display of the same 2D ultrasound monitor of a commercially available needle, which is marketed as an echogenic needle, in the same Blue Phantom™ ultrasound training model tissue block as described above in connection with FIGS. 2A-2D and 2E-2H. It is seen upon viewing FIGS. 3A-3E that the bare needle is much less visible than the needle shown in FIGS. 2A-2H, and it is seen upon viewing FIG. 3F that the commercially available echogenic needle is much less visible than the needles shown in FIGS. 2A-2H.

Figure 4:
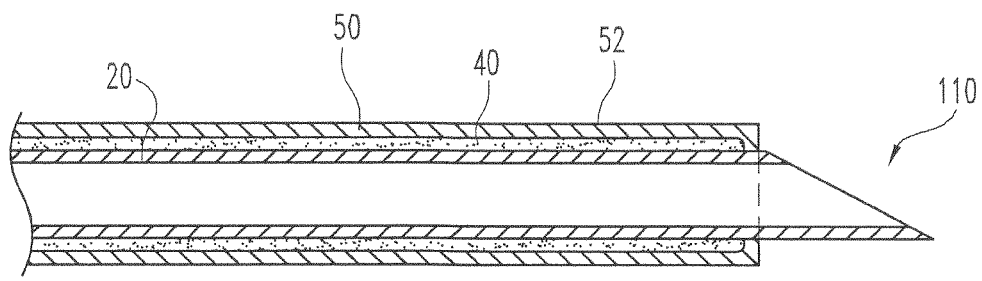
FIG. 4 is a longitudinal cross section elevation view of another hyperechogenic needle embodiment.

In another embodiment, depicted in FIG. 4, needle 110 includes rigid shaft 20 and hyperechogenic particulate material 40, and also includes polymeric coating 50 positioned over at least a portion of shaft 20. In the embodiment shown in FIG. 4, particulate material 40 is positioned between shaft 20 and polymeric coating 50. Polymeric coating 50 has a lubricious external surface 52. As used herein, the term "lubricious" when used in connection with a surface means that the surface is sufficiently smooth to allow for a relatively low coefficient of friction between the needle and the tissue it is penetrating, which improves the ease with which needle 110 passes into and through tissue, and decreases the pain and tissue trauma associated with its use. Needle 110 optionally can also include a friction lowering material (not shown) affixed to external surface 52. Suitable friction lowering materials that are contemplated for use include, for example, PTFE. In another embodiment, the friction lowering material is an agent provided as a coating over polymeric coating 50, over hyperechogenic material 40 or over hyperechogenic layer 260 to reduce the coefficient of friction between the needle and the tissue it is penetrating (i.e., to increase the slipperiness of the needle's surface). One example of a friction lowering material that can be used in this manner is silicone. While not being bound by any theory, it is believed that the ultrasound beam passes through the polymeric material and the friction lowering material, if present, and reflects off the hyperechogenic particulate material back to the ultrasound head.

In one embodiment, polymeric coating 50 comprises a biocompatible polymeric material that is stable under conditions encountered during manufacture and use of the needle, and is effective to provide a boundary between hyperechogenic particulate material 40 and the environment of needle 110. For example, in one embodiment, polymeric coating 50 comprises polytetrafluoroethylene (PTFE) (trade name Teflon™). In another embodiment, the polymeric coating 50 comprises polyethylene terephthalate (PET). In another embodiment, polymeric coating 50 comprises parylene. In this embodiment, parylene can be formed as a relatively thin layer over particulate material 40, such as, for example, as thin as 0.1 microns, which can help to minimize the diameter of needle 110. As will be appreciated by a person of ordinary skill in the art, when the parylene is applied in a layer as thin as this, it will generally conform to the contour of the underlying particulate material 40. Thus, in order to improve the lubricity of the external surface 52 of the parylene layer, a layer having greater thickness can be applied, such as, for example, a layer having a thickness of from about 0.3 to about 1 micron. An even thicker layer, such as a layer up to about 12 microns or larger can be used if desired. In yet another embodiment, polymeric coating 50 comprises at least one of polyurethane, polyethylene, nylon, polyvinyl chloride, polypropylene, polyester, and silicone. In still another embodiment, polymeric coating 50 is at least partially composed of a polyether ether ketone (PEEK). In this embodiment, the durability of the PEEK allows coating 50 to be formed as a relatively thin layer. In certain embodiments described herein, polymeric coating 50 is desirably non-electrically conductive. Thus, in certain embodiments, polymeric coating 50 comprises one or more polymers that impart non-conductivity to coating 50.

Application of polymeric coating 50 can be accomplished using a variety of coating techniques, including but not limited to, powder coating; spray coating; extrusion coating; chemical vapor deposition; spin coating; dip coating; injection molding and curing by applying energy, such as, for example, application of light, heat or chemical energy; injection of one-phase or two-phase self-curing materials; growth of an organic layer, and the like. Various coating processes and systems are known to persons skilled in the pertinent art, and a wide variety of same can be used in connection with application of polymeric coating 50 as described herein. In one preferred manner of applying the coating, the coating is applied using a powder coating technique. Powder coating can be used to provide a coating having a smooth, texture-free surface. By varying the process conditions, however, powder coating techniques can also be used to apply a coating having a textured surface, such as, for example, a surface having a texture commonly referred to as an "orange peel" texture due to the resemblance of the texture to the bumpy surface of the skin of an orange or other citrus fruit. Such an orange peel texture, or other surface texture is included as a feature of the coating in certain embodiments of the present application.

Figure 5:
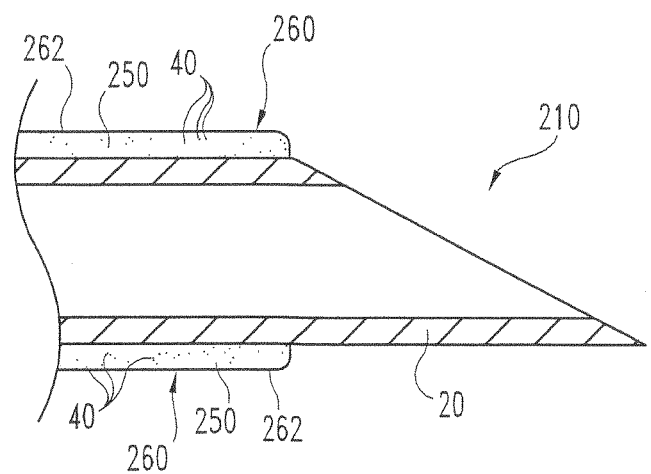
FIG. 5 is a longitudinal cross section elevation view of yet another hyperechogenic needle embodiment.

In the embodiment depicted in FIG. 5, which is a preferred embodiment of the embodiment depicted in FIG. 1, needle 210 includes rigid shaft 20, hyperechogenic particulate material 40 and a polymeric material 250, which can be composed of a thermoplastic polymer resin, such as, for example, the polymers as described above in connection with polymeric coating 50. In this embodiment, particulate material 40 is dispersed in polymeric material 250 to provide hyperechogenic layer 260 in which polymeric material 250 operates as a matrix or scaffold in which particulate material 40 is embedded. In one embodiment, hyperechogenic particulate material 40 has a density that is different from that of polymeric material 250. While the embodiment depicted in FIG. 5 shows hyperechogenic layer 260 extending in the distal direction only to a point that is proximal of the bevel tip, this is not intended to be a limiting feature of the application, it being understood that in alternate embodiments hyperechogenic layer extends distally to a different point. Indeed, in one preferred embodiment, hyperechogenic layer 260 covers the entire needle shaft, including the tip.

Hyperechogenic layer 260 has a lubricious external surface 262 to allow for a relatively low coefficient of friction between needle 210 and the tissue it is penetrating, which improves the ease with which needle 210 passes into and through tissue, and decreases the pain and tissue trauma associated with its use. Needle 210 optionally can also include a friction lowering material (not shown) affixed to external surface 262, which friction lowering material can be, for example, an agent such as silicone provided as a coating over polymeric coating 50 or an agent that is mixed into polymeric coating 50. While not being bound by any theory, it is believed that the ultrasound beam passes through the polymeric material and the friction lowering material, if present, and reflects off the hyperechogenic particulate material back to the ultrasound head.

Particulate material 40 may be interspersed throughout hyperechogenic layer 260 in a uniform pattern or non-uniform manner. For example, it may be more cost-effective if the particles composing the particulate material 40 vary considerably in size, as opposed to maintaining a narrow size range for the particles. Particulate material 40 can be simply mixed into the starting materials used to form polymeric material 250 such that particulate material 40 is randomly dispersed throughout polymeric material 250 in hyperechogenic layer 260 when it is applied to shaft 20. In one manner of applying hyperechogenic layer 260 to shaft 20, particulate material 40 and a suitable polymeric material 250, preferably a thermoplastic polymer material, are simultaneously applied to the surface of shaft 20 using a powder coating technique. Briefly, the powder coating method includes providing a fine powder mixture that includes the hyperechogenic particulate material and the polymeric material, application of the mixture to the shaft of a properly prepared needle, and heating the mixture to melt the polymeric mixture and form a uniform film with the particulate material entrained therein.

The fine powder mixture used in the powder coating application can be provided by mixing a selected particulate material 40 into a selected starting polymeric material, such as, for example, beads or pellets of the selected starting polymeric material, which mixture is then baked and processed into a powder form. For example, the powder form can be made by placing a mixture of the selected particulate material and the selected starting polymeric material into an extruder where it is heated and extruded, followed by rolling the extruded mixture in a flat sheet that is then cooled and broken into small chips. The chips can then be milled and sieved to make a fine powder. In an alternative manner of providing a fine powder mixture for powder coating, a hyperechogenic particulate material in a fine powder form can simply be mixed with a polymeric material in fine powder form. The powder form of the mixture (whether provided by the extrusion and milling approach or by a simple mixing approach) can be applied to shaft 20 using a powder coating method, examples of which are well known to a person of ordinary skill in the art, thereby forming hyperechogenic layer 260. For example, and without limitation, after the needle shaft to be coated is prepared, the powder coating can be applied to the surface of the shaft by spraying the powder using an electrostatic gun, which imparts a positive electric charge on the powder. With the needle shaft grounded, positively charged powder particles are sprayed toward the needle by mechanical or compressed air spraying, and then accelerated toward the workpiece by the electrostatic charge. The needle shaft is then heated, and the powder melts into a uniform film with particulate material entrained therein. When the needle shaft is thereafter cooled, the film hardens to provide hyperechogenic layer 260 on the surface of the needle shaft.

In one embodiment, hyperechogenic layer 260 includes polyethylene terephthalate and a particulate talc material that has a median average particle size of about 9 microns, such as, for example, EliteTalc™ 3000 USP talc, which is commercially available from Cimbar Performance Minerals (Cartersville, Ga.), in which the talc is present at a concentration of about 10 to about 25 weight percent. The PET/talc mixture is preferably applied to the surface of the needle in this embodiment using a powder coating technique. Such a hyperechogenic layer is particularly well suited for a use on a 21 or 22 gauge needle. In another embodiment, hyperechogenic layer 260 includes polyethylene terephthalate and a particulate talc material that has a median average particle size of about 3.8 microns, such as, for example, EliteTalc™ 4000 USP talc, which is commercially available from Cimbar Performance Minerals (Cartersville, Ga.), in which the talc is present at a concentration of about 10 to about 25 weight percent. In one implementation of this embodiment, the talc is present at a concentration of about 10 to about 20 weight percent, more preferably about 15 weight percent, and the PET/talc mixture is preferably applied to the surface of the needle using a powder coating technique.

In an embodiment in which needle 210 is to be used as a nerve blocking needle, it is preferred that the hyperechogenic particulate material be of a type that is electrically non-conductive, or substantially non-conductive so that particulate material 40 does not significantly impair the electrically insulative properties of polymeric material 250 in layer 260. In this regard, a particulate talc material has been found to be substantially nonconductive, allowing it to be a suitable particulate material in this embodiment.

A needle that includes a hyperechogenic particulate material as described in connection with the various embodiments herein may be in a wide variety of shapes and sizes. For example, representative needles may be constructed to have a wide variety of forms and to operate in a wide variety of ways, including but not limited to the commonly-known forms useful as biopsy needles, ablation probes, needles used to implant treatment therapies, such as, for example, implant devices, radioactive seed implants or drugs, and needles used in blocking peripheral nerves. In addition, the disclosures provided herein are contemplated to be suitable for other types of devices or components that can be suitably modified to include hyperechogenic particulate materials. For example, other medical devices for which real-time imaging would be useful include stents, stylets, and the like, or softer, more flexible devices or components thereof, such as, for example, flexible catheters and the like. Other components that can be suitably modified as described herein include supporting bands or outer sheaths for use in connection with such medical devices.

In another embodiment, a therapeutic agent, such as, for example, a drug or bioactive agent, is included with the hyperechogenic particulate material and/or in the polymeric coating 50 or polymeric material 250 to impart biological properties to the surface of the needle or other medical device. In embodiments in which the needle includes a friction lowering material affixed to the external surface of a polymeric coating or hyperechogenic layer, the therapeutic agent can be included in the friction lowering material. Whether present in a hyperechogenic particulate material, a polymeric coating, a hyperechogenic layer or a friction lowering material, the therapeutic agent can be released over time as the needle is positioned in contact with tissue or fluid.

A wide variety of therapeutic agents can be included provided that it does not interfere with the required characteristics and functions of the needle. The term "bioactive agent" includes, but is not limited to, proteins, enzymes, enzyme inhibitors, immunological molecules, hormones, neurotransmitters, peptides, lipids, nucleic acids, sugars, carbohydrates, glycoproteins, lectins, bacteria, viruses, replication inhibitors, proteases, antibiotics, antifungals, bacteriostatic compounds, toxins, microbials, anti-microbials, growth factors, angiogenic factors, nutrients, and vitamins. Examples of suitable drugs or bio-active agents include, for example, without limitation, thrombo-resistant agents, antibiotic agents, anti-tumor agents, anti-viral agents, anti-angiogenic agents, angiogenic agents, anti-inflammatory agents, cell cycle regulating agents, their homologs, derivatives, fragments, pharmaceutical salts and combinations thereof.

Useful thrombo-resistant agents can include, for example, heparin, heparin sulfate, hirudin, chondroitin sulfate, dermatan sulfate, keratin sulfate, lytic agents, including urokinase and streptokinase, their homologs, analogs, fragments, derivatives and pharmaceutical salts thereof.

Useful antibiotics can include, for example, penicillins, cephalosporins, vancomycins, aminoglycosides, quinolones, polymyxins, erythromycins, tetracyclines, chloramphenicols, clindamycins, lincomycins, sulfonamides, their homologs, analogs, fragments, derivatives, pharmaceutical salts and mixtures thereof.

Useful anti-tumor agents can include, for example, paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; enzymes including asparaginase; and hormones including tamoxifen and flutamide; their homologs, analogs, fragments, derivatives, pharmaceutical salts and mixtures thereof.

Useful anti-viral agents can include, for example, amantadines, rimantadines, ribavirins, idoxuridines, vidarabines, trifluridines, acyclovirs, ganciclovirs, zidovudines, foscarnets, interferons, their homologs, analogs, fragments, derivatives, pharmaceutical salts and mixtures thereof.

As indicated above, one particularly useful embodiment of a needle having a hyperechogenic particulate material affixed thereto as described herein is a needle used for peripheral nerve blockage in a regional anesthesia application that is configured to create electrical current at its tip for nerve stimulation. It is a well known medical practice to produce regional anesthesia in a patient by depositing a local anesthetic along the path of one or more peripheral nerves. The success of the technique is largely dependent upon the ability of the clinician to deposit a local anesthetic in close proximity to the nerve without causing trauma to the nerve as may result from contacting the needle directly with the nerve. Local anesthetics comprise a class of drugs which reversibly interact with a nerve in a manner such that the propagation of signals along the nerve fiber is significantly reduced, or stopped altogether. When such drugs are deposited along large nerve trunks, such as the femoral nerve in the groin or the nerve trunk of the brachial plexus in the axilla or neck, the effect is to make the targeted body structure, such as a body limb, insensate or "numb." This phenomena is similar to that experienced by a patient at a dentist's office when local anesthetics are used for placement of tooth fillings.

When the local anesthetic is intended to be injected into the groin, neck or axilla, the relevant nerve or nerves must, of course, be located before the injection is given. A general understanding of surface anatomy allows the general area of the nerve to initially be located. Historically the nerve was located by eliciting a paraesthesia, or pain, resulting from the needle coming into contact with the nerve fiber. This is very similar to the sensation experienced by hitting the "crazy bone," where the ulnar nerve is stimulated by pressure being placed on it between the skin and the bone. When this process is done with a needle, however, the risk of damaging a nerve fiber is high, with the possible result of permanent nerve injury. This technique has been largely abandoned due to the high possibility of such permanent injury.

The use of nerve blocks to accomplish such anesthesia has now progressed to the point where a stimulating needle may be utilized to locate a nerve, without making direct contact with the nerve. Nerve block systems are provided with certain features to minimize damage to the nerve. A first feature is to cut the needle end with a "B" bevel, at an angle of roughly 45°. This action produces a lowered incidence of impinging nerve fibers when the needle is directed at a nerve trunk. This needle angle tends to allow nerve fibers to roll out of the way, as opposed to more common sharp tips seen in needles of the type that are used to puncture skin for the introduction of, e.g., solutions or catheters below the skin. A second feature is to provide the needle with a coaxial design, consisting of a needle shaft covered with a plastic coating, such as, for example, PEEK or PTFE. The needle shaft is connected to an electrode, and the needle electrode system and a grounding electrode (also referred to as a "skin electrode") are connected to a commercially available nerve stimulation box.

An electrical circuit is formed when the needle is placed in the patient's tissue and the grounding electrode is connected to the patient's skin, for example, with a conventional EKG electrode. This circuit is capable of delivering adjustable pulses of electrical energy through the needle, through the patient's tissues, and to the skin electrode. When the needle tip is in close proximity to the nerve, the motor nerve fibers are stimulated to cause muscles innervated by the nerve to twitch by electrical stimulation resulting from the electrical current flow in the electrical circuit. In this nerve stimulation technique, the clinicians are, in effect, attempting to localize the nerve without actually contacting the nerve fibers in a manner that might cause permanent damage to the nerve.

Needle insertion by the aforementioned technique is based upon clinical judgment, and therefore, is not precise. The amount of electric current necessary to make the correct muscle twitch for the nerve to be blocked is determined by the proximity of the needle to the nerve. Generally, only a small amount of current is required, since resistance is typically minimal as the needle approaches the nerve. In clinical practice, this is typically performed at 1 to 2 Hz stimulation frequency, with an optimal current of 1.0 milliamps or less to bring the needle in close enough proximity to the nerve for drug injection. The actual voltage required is a property of the particular peripheral nerve stimulator utilized in the technique. It is set at a value to produce a motor response without pain.

To further improve accurate placement of the tip of a never block needle, the electrical current stimulation discussed above can be used together with 2D ultrasound equipment to allow the practitioner to visualize the needle and the target nerve bundle prior to and during insertion of the needle to more precisely locate the nerve under the skin prior to and during insertion of the needle. Nerve block needle embodiments are described herein that include a hyperechogenic particulate material to enhance the ultrasound imaging characteristics of a nerve block needle.

Figure 7:
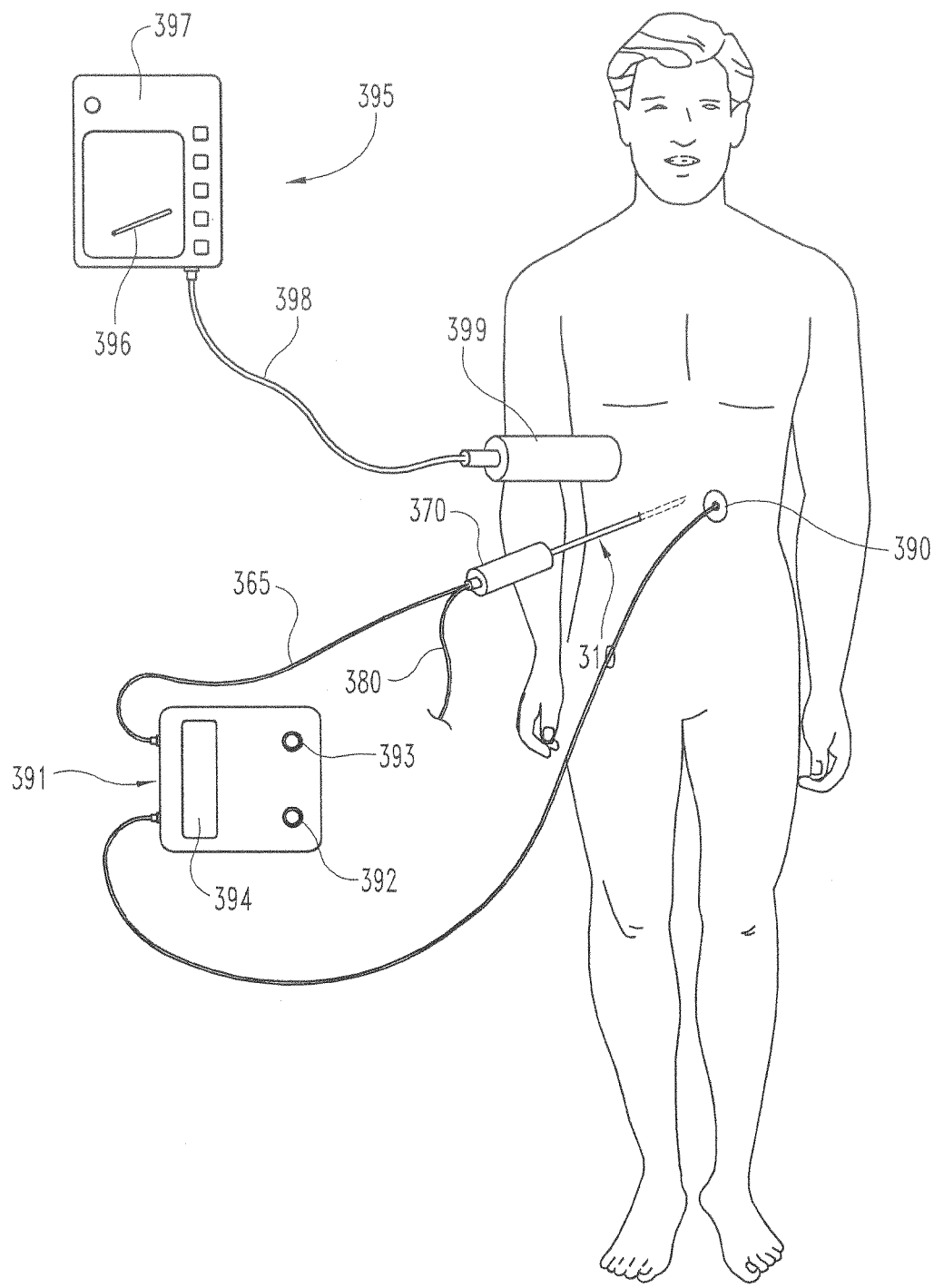
FIG. 7 is a schematic perspective view of a system embodiment for accurately positioning the distal end of a hyperechogenic nerve block needle.

With reference to FIG. 6, nerve block needle 310 includes inner shaft 20, which is made of a conductive material, for example, a conductive metal or metal alloy, such as surgical grade steel. Polymeric coating 50 covers most of the length of the shaft, and extends generally from the proximal end 23 of the needle nearly to the bare metal needle tip portion 25 of the distal end 24 of the needle, leaving only the tip portion 25 uncovered. Positioned between shaft 20 and polymeric coating 50 is hyperechogenic particulate material 40, which can be affixed to shaft as described above. In an alternate embodiment (not shown), polymeric coating 50 and the layer of hyperechogenic particulate material 40 positioned between shaft 20 and polymeric coating 50 are replaced by a hyperechogenic layer having a particulate material 40 dispersed in a polymeric material, as described hereinabove with respect to hyperechogenic layer 260. In one embodiment, discussed hereinabove, the hyperechogenic layer can be applied using a powder coating technique, and can cover the entire tip portion of shaft 20. Hyperechogenic particulate material 40 enhances the reflection of ultrasound waves toward an emitter receiver array of a 2D ultrasound machine (not shown), thereby allowing enhanced needle visualization with a 2D ultrasound machine. This allows needle 310 to be inserted into the patient's tissue and advanced toward a peripheral nerve with greater precision than may be achieved with either ultrasound or peripheral nerve stimulation alone. Also affixed to shaft 20 of needle 310 is conductive hub 360, which is in direct contact with shaft 20 to allow for electrical current to pass from hub 360 to shaft 25. Wire 365 is affixed at its distal end to hub 360, also in direct contact to allow for electrical current to pass from wire 365 to hub 360. The proximal end of wire 365 is connected to a source of electrical current (such as, for example, electrical stimulation device 391 as shown in FIG. 7). For example, the proximal end of wire 365 may terminate at a mechanical connector (not shown) of a type that is suitable for connection to an outlet of the peripheral nerve stimulator 391 or other source of electrical current.

In one embodiment, needle tip portion 25 of the hyperechogenic stimulating block needle 310 is bevel cut at an angle of approximately 45°, or in other words, at a less acute angle than a standard needle. Encasing hub 360 is insulating enclosure 370, which can be composed of a plastic or other electrically insulating material. Also affixed to proximal end 23 of shaft 20 in fluid communication with lumen 30 of shaft 20 is conduit 380, which can be used to deliver a local anesthetic drug to lumen 30 of shaft 20 for injection of the drug through lumen 30 when deemed appropriate by a medical care provider using needle 310. Conduit 380 is sized and shaped for attachment to a syringe, tube, or other drug delivery device in well known fashion. Needle 310 can be utilized to deposit drugs near a nerve, e.g., to produce local or regional anesthesia at a targeted area in the body of the patient. Thus, among other uses, needle 310 may be utilized in a process for blocking a peripheral nerve that combines nerve stimulation and 2D ultrasound visualization techniques.

Polymeric coating 50 is composed of a polymer material that is substantially electrically non-conducting. Leaving tip portion 25 bare allows for an electrical current to be passed to tip portion 25 of the needle and through the surrounding tissue to grounding electrode 390 (also referred to as "skin electrode"), as depicted in FIG. 7. This type of needle construction ensures maximal current density, as the current can only exit at the uncovered metal needle tip. The needle is connected at its proximal end to wire 365 (also referred to as "needle electrode 365"). Needle electrode 365 and a grounding electrode 390 are then connected to battery powered electrical stimulation device 391 (also referred to as "peripheral nerve stimulator 391"). In the embodiment shown in FIG. 7, peripheral nerve stimulator 391 has two controls, namely a frequency control knob 392, and an amperage or current control knob 393. Also, in the example shown, peripheral nerve stimulator 391 is provided with an optional digital readout 394 for displaying the current when a circuit is formed.

Polymeric coating 50 insulates shaft 20 from the remaining patient tissue, ensuring that electrical current primarily exits at the needle tip portion 25. After needle 310 is introduced into the skin of a patient, an electrical circuit is formed between the needle tip portion 25 and grounding electrode 390. When needle tip portion 25 comes in close proximity to a nerve, the electrical current will cause the nerve to depolarize, subsequently inducing the corresponding muscle innervated by this nerve to twitch. Electrical stimulation device 391 can be adjusted from 5.0 mA down to approximately 0.3 mA. The closer needle tip portion 25 is to the nerve, the less current is needed to depolarize the nerve. This allows the practitioner to adjust needle placement with electrical stimulation for optimal positioning relative to the target nerve while minimizing the risk of nerve damage. The practitioner will then deposit a local anesthetic solution through the needle and into the area surrounding the nerve. The local anesthetic solution will block nerve impulses traveling to and from the brain to the area the nerve innervates, thereby achieving the desired local numbing.

In a method for guided positioning of a nerve blocking needle, such as nerve blocking needle 310 described above, the target tissue position is a position near a peripheral nerve to be blocked, and as the needle is advanced toward the target peripheral nerve, not only does the clinician view the real-time position of the needle relative to the nerve using a 2D ultrasound apparatus, but the clinician also controls peripheral nerve stimulator 391 to emit DC current through the distal portion of the needle at a predetermined voltage that is determined according to the characteristics of the peripheral nerve stimulator.

More specifically, as nerve block needle 310 is inserted into patient tissue, a pathway is thereby formed for electrons to flow from peripheral nerve stimulator 391 through needle electrode 365 to the nerve block needle 310, and through the shaft 20 (which is electrically insulated from the patient) and the tip portion 25 of needle 310. The electrons pass through the patient's tissue and exit the patient's tissue through skin electrode 390, returning to peripheral nerve stimulator 391 via grounding electrode 390. The target peripheral nerve is located by activating the peripheral nerve stimulator 391 to form the circuit. Stimulator frequency knob 392 is adjusted to emit an electrical pulse, most commonly with a range of 1 to 2 Hz. Stimulator amperage control knob 393 is adjusted to elicit a motor response when the needle is advanced in the region of the target peripheral nerve. The amperage is commonly set at about 1.0-2.0 milliamps to search for the general nerve location.

The nerve block needle 310 is advanced toward the target peripheral nerve using general knowledge of surface anatomy, and with the guidance of the 2D ultrasound apparatus 395. As the nerve block needle 310 is advanced toward the target peripheral nerve, the motor response is elicited by stimulation of the motor nerve fibers by current flowing through the nerve. The correct nerve to be blocked can be determined by a general understanding of the anatomy of the nervous system, and in particular, by recognizing which nerve will cause a specific part of the body to move as a result of the electrical stimulation. The motor response is different for each nerve to be blocked. As the needle is advanced toward the target nerve, the motor response becomes more intense, since less tissue is present between the needle tip portion 25 and target peripheral nerve, thereby reducing the resistance to current flow. The current is decreased as the needle approaches the nerve, as less current is required to elicit a motor response. When the clinician observes that a current of 1.0 milliamps or less elicits a motor response, a determination is made that the needle tip is in close enough proximity to the nerve, and injects a local anesthetic, thereby achieving the desired clinical response of making the area innervated by the nerve insensitive or numb.

FIG. 7 illustrates a system for peripheral nerve block that can be used in this method. The system includes a hyper-echogenic stimulating block needle 310, a 2D ultrasound apparatus 395, and a peripheral nerve stimulator 391. In a particular method for positioning needle 310 in a specific target location in soft tissue, needle 310 is advanced toward the target location using general knowledge of surface anatomy, and with the guidance of 2D ultrasound apparatus 395, which includes monitor 396, computer 397, head cord 398 and ultrasonic head 399. Ultrasonic head 399 typically includes a series of piezoelectric effect crystals in alignment. Ultrasound head 399 is capable of sending out a series of ultrasound beams, and to receive reflected energy. The reflected energy is amplified, processed, and integrated in 2D ultrasound apparatus 395, thereby rendering a 2D planar image of the tissue below the head, which is displayed on monitor 396. The target soft tissue location is rendered visible relative to surrounding structures in a lateral and axial fashion in the plane of the 2D ultrasound apparatus 395. The signal from ultrasound machine head 399 is received by computer 397 via 2D ultrasound head cord 398.

The ability to see the needle path and the target peripheral nerve to be blocked, in combination with peripheral nerve stimulation, allows the target peripheral nerve to be approached with more precision than has previously been possible. The position of the needle can be resolved anatomically using 2D ultrasound by simultaneous visibility of the needle path and the target peripheral nerve, and can be resolved physiologically by using peripheral nerve stimulation to elicit a motor response by minimizing the current. This allows the needle tip portion 25 to be directed to a closer proximity to the peripheral nerve when compared to the use of peripheral nerve stimulation alone, or the use of 2D ultrasound and peripheral nerve stimulation using a needle without hyperechogenic particulate material. As a result, drugs can be deposited more easily and precisely than has previously been possible.

A nerve block needle having a general configuration as set forth in FIGS. 6 and 7 can alternatively have a form corresponding to the embodiment depicted in FIG. 5, in which hyperechogenic particulate material 40 is embedded in a polymeric material 250 to form a hyperechogenic layer 260. In this embodiment, hyperechogenic layer 260 covers the length of the shaft. In one embodiment, the tip is left uncovered. In another embodiment, the tip is covered with the hyperechogenic layer 260. In this embodiment, hyperechogenic layer 260 is electrically insulative. It is within the skill of a person skilled in the art to select a suitable polymeric material and a suitable hyperechogenic particulate material to achieve adequate electrical insulative properties for this embodiment. It is desirable in these embodiments that polymeric coating 50 and polymeric material 250 be composed of a highly durable and electrically insulative material, such as, for example, PEEK, PTFE, PET or parylene.

Thus, as exemplified by the method embodiment described in detail above, one aspect of the present invention includes a method of guided placement of a needle tip using an ultrasonic imaging apparatus. This method includes providing a needle that includes a rigid shaft having a longitudinal axis, a proximal end, a distal end, and an outer surface extending from the proximal end to the distal end, the distal end including a tip portion defining a point, and a hyperechogenic particulate material affixed to the shaft along at least a portion of the outer surface, the hyperechogenic particulate material being operable in response to a beam of ultrasound waves in a two-dimensional ultrasound plane to produce an image of the needle, even when the needle is in a position forming a non-90° angle between the longitudinal axis and the direction of the ultrasound waves in the two-dimensional ultrasound plane, thereby enhancing the ultrasonic imaging characteristics of the needle; inserting the needle into soft tissue of a patient; visualizing the needle with a two-dimensional ultrasound imaging apparatus; and manipulating the needle tip to a desired location in the tissue under real-time two-dimensional ultrasound imaging. The needle can be of a wide variety of forms and configurations, many embodiments of which are described herein and shown in the drawings.

In various alternative aspects, the present specification contemplates methods for ultrasonically imaging a wide variety of hyperechogenic needles not limited to nerve block needles, and methods for ultrasonically imaging a hyperechogenic medical device other than a needle in biological tissue. In one embodiment, the method includes providing a device having a hyperechogenic particulate material affixed to an outer surface of the device; and inserting the hyperechogenic medical device into the tissue of a patient under two-dimensional ultrasound imaging. More particularly, the method includes directing an ultrasonic beam toward the hyperechogenic device during the inserting and receiving an ultrasound image produced by the particulate material in response to the ultrasonic beam.

Another aspect of the present invention includes manufacturing a hyperechogenic needle for insertion into biological tissue and imageable with ultrasonic imaging equipment. In one embodiment, the method includes providing a rigid shaft formed of a material such as stainless steel or plastic, the shaft having an inner surface defining a lumen therethrough, an outer surface, a proximal end and a distal end defining a distal tip portion that includes a sharp tissue-penetrating point; and affixing a hyperechogenic particulate material onto at least a portion of the outer surface of the shaft. The particulate material can be affixed to the shaft, for example, using an adhesive or resin as described above. In another embodiment, after the particulate material is affixed to the shaft, a polymeric coating is applied over the particulate material to provide a barrier between the particulate material and the needle's environment. The polymeric coating can be applied in a wide variety of ways as would occur to a person skilled in the art, and as described above.

In making a hyperechogenic needle in which the hyperechogenic particulate material is embedded in a polymeric material, the needle can be made by providing a rigid shaft as described above; positioning the shaft in an extruder or injection mold; providing a mixture of plastic pellets and hyperechogenic particulate material; and feeding the mixture to the extruder or injection mold effective to melt the plastic pellets, mix the particulate material into the molten plastic, and apply the molten mixture to the shaft for hardening to provide a hyperechogenic needle. Mixing of the plastic pellets and the particulate material can be achieved, for example, using a mixer operable to gravity feed the parts to be mixed into a screw or worm-gear type mechanism well known in extruder machines and other plastic manufacturing equipment. Before, during or after the mixing, the mixture may be heated to maintain the mixture in a molten or liquid state allowing it to be formed to the desired shape. Alternatively, the mixture of hyperechogenic particulate material and polymeric material can be applied to the surface of a needle using a powder coating process, examples of which are well known and understood by a person of ordinary skill in the art.

While various plastic processing techniques are described above, it is not intended that the present application be limited to these techniques, it being understood that a wide variety of other techniques are known and can be employed for applying a plastic coating to a device as described herein, or to apply a hyperechogenic layer that includes a particulate material dispersed in a polymeric material. Non-limiting examples of such other techniques include spray coating; chemical vapor deposition; spin coating; dip coating; and curing by applying energy, such as, for example, application of light, heat or chemical energy to a precursor material positioned on the needle shaft; self-curing of one-phase or two-phase materials, and the like.

In one embodiment, a rigid shaft comprising surgical grade steel is coated with a hyperechogenic particulate material comprising talc and calcium carbonate using a resin. In one embodiment, the coating comprises from 0 to about 70 weight percent talc, from 0 to about 70 weight percent calcium carbonate and from about 30 to about 60 weight percent resin. In another embodiment, the coating comprises from 30 to about 60 weight percent talc, from 1 to about 25 weight percent calcium carbonate and from about 30 to about 60 weight percent resin. In yet another embodiment, the coating comprises from 35 to about 50 weight percent talc, from 5 to about 15 weight percent calcium carbonate and from about 30 to about 60 weight percent resin. In still another embodiment, the coating comprises from about 5 to about 70% talc and from about 30 to about 95% resin. Any of the coating compositions described herein may also include, but does not necessarily include, a resin solvent. Over the particulate material coating is placed a polymeric coating, such as, for example, a parylene coating or a PET coating. In another embodiment, the particulate material is dispersed in the polymeric coating, such as, for example, a PET coating. In some embodiments, it may be necessary or desired to include a primer over the hyperechogenic particulate material to improve adherence of the polymeric coating thereto.

The terminology used herein is for the purpose of describing particular embodiments only and is not intended to limit the scope of the present application. Throughout this description, the expressions "polymeric coating" or "polymeric material" are used to denote any suitable biocompatible polymer. Exemplary polymeric materials include, but are not limited to, thermoplastic polymers, thermoset polymers, elastomers, adhesives, resins, sealants, and composites thereof. Moreover, the expression "rigid shaft" is intended to encompass a variety of materials that are suitable for a given medical use, and include a wide range of materials such as polymeric materials, metals and ceramics. However, in an embodiment in which the rigid shaft is electrically conductive, it will be appreciate that the shaft will typically be made of a metal. Exemplary metals that can be employed include medical grade stainless steel, titanium or titanium alloy. The expression "soft tissue" is used herein to refer to any host tissue other than bone. The particulate material used may meet all of the United States Pharmacopoeia requirements for chemical and biological purity. The particulate material may also conform to the requirements of the Cosmetic Manufacturer's Association for maximum limits on arsenic, lead, and heavy metals.

While multiple embodiments are described herein in which the particulate material 40 comprises a particulate talc material and/or a particulate calcium carbonate material and the like, it is to be understood that embodiments with these materials are exemplary, and it is not intended that the present application be limited thereto, it being understood that a variety of other materials can be used that have similar ultrasound imaging properties as described herein. For example, in another embodiment, particulate material 40 comprises particulate wollastonite material. The hyperechogenic particulate material can have a variety of sizes and shapes. For example, in one embodiment, the hyperechogenic particulate material has an average median size of from about 1 to about 18 microns.

As will be appreciated from the above descriptions, the present application discloses a variety of embodiments and aspects, nonlimiting examples of which include:

1. A needle effective for guided positioning in soft tissue of a patient with the aid of a real-time two-dimensional ultrasonic imaging apparatus, the needle comprising:
a rigid shaft having a longitudinal axis, a proximal end, a distal end, and an outer surface extending from the proximal end to the distal end, said distal end including a tip portion defining a point;
a hyperechogenic layer affixed to said shaft along at least a portion of the outer surface;
wherein said hyperechogenic layer comprises a polymeric material having a hyperechogenic particulate material dispersed therein;
wherein said hyperechogenic particulate material is operable in response to a beam of ultrasound waves in a two-dimensional ultrasound plane to produce an image of said needle when said needle is in a position forming a non-90° angle between the longitudinal axis and the direction of the ultrasound waves in the two-dimensional ultrasound plane, thereby enhancing the ultrasonic imaging characteristics of the needle; and
wherein said hyperechogenic particulate material comprises a particulate talc material.

2. The needle in accordance with embodiment 1 wherein said hyperechogenic particulate material further comprises a member selected from the group consisting of a particulate calcium-containing material, a silicate, a mineral including calcium, barium, aluminum or magnesium, graphite, silica and a carbonate, sulfate, oxide, hydroxide or phosphate of calcium, magnesium, barium or aluminum.

3. The needle in accordance with embodiment 1 or embodiment 2 wherein said polymeric material comprises a thermoplastic polymer material.

4. The needle in accordance with embodiment 1 or embodiment 2 wherein said polymeric material comprises a member selected from the group consisting of polyurethane, polyethylene, nylon, polytetrafluoroethylene, polyvinyl chloride, polypropylene, polyester, parylene, silicone and polyethylene terephthalate 5. A needle effective for guided positioning in soft tissue of a patient with the aid of a real-time two-dimensional ultrasonic imaging apparatus, the needle comprising:
a rigid shaft having a longitudinal axis, a proximal end, a distal end, and an outer surface extending from the proximal end to the distal end, said distal end including a tip portion defining a point;
a hyperechogenic particulate material affixed to said shaft along at least a portion of the outer surface, said hyperechogenic particulate material operable in response to a beam of ultrasound waves in a two-dimensional ultrasound plane to produce an image of said needle when said needle is in a position forming a non-90° angle between the longitudinal axis and the direction of the ultrasound waves in the two-dimensional ultrasound plane, thereby enhancing the ultrasonic imaging characteristics of the needle; and
a polymeric coating positioned over at least a portion of said shaft and covering said hyperechogenic particulate material, the polymeric coating having a lubricious external surface;
wherein said hyperechogenic particulate material comprises a particulate talc material.

6. The needle in accordance with embodiment 1 or embodiment 5 or embodiment 9 or embodiment 33 or embodiment 34 wherein said particulate talc material has an average particle size of from about 2 to about 18 microns.

7. The needle in accordance with embodiment 1 or embodiment 5 or embodiment 9 or embodiment 33 or embodiment 34 wherein said particulate talc material comprises platy talc.

8. The needle in accordance with embodiment 1 or embodiment 5 wherein said polymeric coating comprises polyethylene terephthalate.

9. A needle effective for guided positioning in soft tissue of a patient with the aid of a real-time two-dimensional ultrasonic imaging apparatus, the needle comprising:
a rigid shaft having a longitudinal axis, a proximal end, a distal end, and an outer surface extending from the proximal end to the distal end, said distal end including a tip portion defining a point;
a hyperechogenic particulate material affixed to said shaft along at least a portion of the outer surface, said hyperechogenic particulate material operable in response to a beam of ultrasound waves in a two-dimensional ultrasound plane to produce an image of said needle when said needle is in a position forming a non-90° angle between the longitudinal axis and the direction of the ultrasound waves in the two-dimensional ultrasound plane, thereby enhancing the ultrasonic imaging characteristics of the needle; and
a polymeric coating positioned over at least a portion of said shaft and covering said hyperechogenic particulate material, the polymeric coating having a lubricious external surface;
wherein said hyperechogenic particulate material comprises a member selected from the group consisting of a particulate talc material, a particulate calcium-containing material, a silicate, a mineral including calcium, barium, aluminum or magnesium and a carbonate, sulfate, oxide, hydroxide or phosphate of calcium, magnesium, barium or aluminum.

10. The needle in accordance with embodiment 9 or embodiment 33 wherein said hyperechogenic particulate material comprises a calcium-containing material.

11. The needle in accordance with embodiment 10 wherein said calcium-containing material comprises particulate calcium carbonate.

12. The needle in accordance with embodiment 11 wherein said particulate calcium carbonate comprises a member selected from the group consisting of ground calcium carbonate and precipitated calcium carbonate.

13. The needle in accordance with embodiment 10 wherein said calcium-containing material comprises a member selected from the group consisting of calcium phosphate and hydroxyapatite.

14. The needle in accordance with embodiment 9 or embodiment 33 wherein said hyperechogenic particulate material comprises a mineral including calcium, barium, aluminum or magnesium.

15. The needle in accordance with embodiment 14 wherein said mineral comprises a member selected from the group consisting of calcite, aragonite, dolomite, barite and hydroxyapatite.

16. The needle in accordance with embodiment 9 or embodiment 33 wherein said hyperechogenic particulate material comprises a silicate.

17. The needle in accordance with embodiment 16 wherein said silicate comprises a member selected from the group consisting of a wollastonite, a talc, a quartz, a phyllosilicate, a montmorillonite, an inosilicate and a tectosilicate.

18. The needle in accordance with embodiment 9 or embodiment 33 wherein said hyperechogenic particulate material comprises a carbonate, sulfate, oxide, hydroxide or phosphate of calcium, magnesium, barium or aluminum.

19. The needle in accordance with embodiment 1 or embodiment 5 or embodiment 9 or embodiment 33 or embodiment 34 wherein the particulate material is a surface coated particulate material.

20. The needle in accordance with embodiment 19 wherein the surface coated particulate material includes a stearic acid coating.

21. The needle in accordance with embodiment 1 or embodiment 5 or embodiment 9 or embodiment 33 or embodiment 34 wherein said shaft comprises surgical grade steel.

22. The needle in accordance with embodiment 1 or embodiment 5 or embodiment 9 or embodiment 33 or embodiment 34 wherein said shaft further includes an inner surface defining a lumen through said shaft.

23. The needle in accordance with embodiment 1 or embodiment 5 or embodiment 9 or embodiment 33 or embodiment 34 wherein at least a portion of said hyperechogenic particulate material is positioned between said shaft and said polymeric coating.

24. The needle in accordance with embodiment 5 or embodiment 9 or embodiment 33 or embodiment 34 wherein at least a portion of said hyperechogenic particulate material is dispersed in said polymeric coating.

25. The needle in accordance with embodiment 1 or embodiment 24 wherein said hyperechogenic particulate material is dispersed in said polymeric coating at a concentration of from about 5 to about 25 weight percent.

26. The needle in accordance with embodiment 1 or embodiment 5 or embodiment 9 or embodiment 33 or embodiment 34 wherein said needle comprises a friction lowering material applied to said lubricious external surface.

27. The needle in accordance with embodiment 1 or embodiment 5 or embodiment 9 or embodiment 33 or embodiment 34 wherein said needle is configured for use in blocking a nerve of a patient using simultaneous electrical nerve stimulation and two-dimensional ultrasound visualization of the nerve; and wherein said polymeric coating composes an insulating layer covering at least a portion of said shaft.

28. The needle in accordance with embodiment 27 wherein said polymeric coating covers at least a portion of said hyperechogenic particulate material.

29. The needle in accordance with embodiment 27 wherein said shaft is electrically conductive, said polymeric layer covers substantially all of said shaft except not said tip portion.

30. The needle in accordance with embodiment 27 wherein said polymeric coating comprises a member selected from the group consisting of polyurethane, polyethylene, nylon, polytetrafluoroethylene, polyvinyl chloride, polypropylene, polyester, parylene and silicone.

31. The needle in accordance with embodiment 27 wherein said polymeric coating comprises a polyethylene terephthalate.

32. The needle in accordance with embodiment 1 or embodiment 5 or embodiment 9 or embodiment 33 or embodiment 34 wherein said tip comprises a bevel.

33. A needle effective for guided positioning in soft tissue of a patient with the aid of a real-time two-dimensional ultrasonic imaging apparatus, the needle comprising:
a rigid shaft having a longitudinal axis, a proximal end, a distal end, and an outer surface extending from the proximal end to the distal end, said distal end including a tip portion defining a point;
a hyperechogenic particulate material affixed to said shaft along at least a portion of the outer surface, said hyperechogenic particulate material operable in response to a beam of ultrasound waves in a two-dimensional ultrasound plane to produce an image of said needle when said needle is in a position forming a non-90° angle between the longitudinal axis and the direction of the ultrasound waves in the two-dimensional ultrasound plane, thereby enhancing the ultrasonic imaging characteristics of the needle; and
a polymeric coating positioned over at least a portion of said shaft and covering said hyperechogenic particulate material, the polymeric coating having a smooth external surface;
wherein said hyperechogenic particulate material has a median average particle size of from about 1 to about 18 microns.

34. A needle effective for guided positioning in soft tissue of a patient with the aid of a real-time two-dimensional ultrasonic imaging apparatus, the needle comprising:
a rigid shaft having a longitudinal axis, a proximal end, a distal end, and an outer surface extending from the proximal end to the distal end, said distal end including a tip portion defining a point;
a hyperechogenic particulate material affixed to said shaft along at least a portion of the outer surface, said hyperechogenic particulate material operable in response to a beam of ultrasound waves in a two-dimensional ultrasound plane to produce an image of said needle when said needle is in a position forming a non-90° angle between the longitudinal axis and the direction of the ultrasound waves in the two-dimensional ultrasound plane, thereby enhancing the ultrasonic imaging characteristics of the needle; and a polymeric coating positioned over at least a portion of said shaft and covering said hyperechogenic particulate material, the polymeric coating having a lubricious external surface;

wherein said hyperechogenic particulate material comprises a member selected from the group consisting of graphite and silica.

35. A system for guided placement of the tip of a needle, comprising:

a needle configured for insertion into soft tissue of a patient, said needle comprising a rigid shaft having a longitudinal axis, a proximal end, a distal end, and an outer surface extending from the proximal end to the distal end, said distal end including a tip portion defining a point;

a hyperechogenic particulate material affixed to said shaft along at least a portion of the outer surface, said hyperechogenic particulate material operable in response to a beam of ultrasound waves in a two-dimensional ultrasound plane to produce an image of said needle when said needle is in a position forming a non-90° angle between the longitudinal axis and the direction of the ultrasound waves in the two-dimensional ultrasound plane, thereby enhancing the ultrasonic imaging characteristics of the needle; and a polymeric coating positioned over at least a portion of said shaft and covering said hyperechogenic particulate material, the polymeric coating having a lubricious external surface;

wherein said hyperechogenic particulate material comprises a member selected from the group consisting of a particulate talc material, a particulate calcium-containing material, a silicate, a mineral including calcium, barium, aluminum or magnesium and a carbonate, sulfate, oxide, hydroxide or phosphate of calcium, magnesium, barium or aluminum; and a two-dimensional ultrasound apparatus capable of visualizing at least a portion of the needle in a segment of tissue of the patient.

36. The system of embodiment 35, wherein the needle is configured for use in blocking a nerve of a patient; wherein said needle shaft is electrically conductive; wherein said polymeric coating is generally non-conductive; wherein said hyperechogenic particulate material extends along at least a portion of a length of said shaft; and wherein the system further comprises a peripheral nerve stimulator capable of electrical connection with the shaft for transmitting an electrical pulse therethrough.

37. The system of embodiment 36, wherein said peripheral nerve stimulator is capable of providing an adjustable current for eliciting a motor response.

38. A method for positioning a needle in soft tissue of a patient with the aid of a real-time two-dimensional ultrasonic imaging apparatus, the method comprising:

providing a needle that includes a rigid shaft having a longitudinal axis, a proximal end, a distal end, and an outer surface extending from the proximal end to the distal end, said distal end including a tip portion defining a point, and a hyperechogenic particulate material affixed to the shaft along at least a portion of the outer surface, the hyperechogenic particulate material being operable in response to a beam of ultrasound waves in a two-dimensional ultrasound plane to produce an image of said needle when said needle is in a position forming a non-90° angle between the longitudinal axis and the direction of the ultrasound waves in the two-dimensional ultrasound plane, thereby enhancing the ultrasonic imaging characteristics of the needle;

inserting the needle into soft tissue of a patient;

visualizing the needle with a two-dimensional ultrasound imaging apparatus; and manipulating the needle tip to a desired location in the tissue under real-time two-dimensional ultrasound imaging;

wherein said hyperechogenic particulate material comprises a member selected from the group consisting of a particulate talc material, a particulate calcium-containing material, a silicate, a mineral including calcium, barium, aluminum or magnesium and a carbonate, sulfate, oxide, hydroxide or phosphate of calcium, magnesium, barium or aluminum.

39. A method for blocking a nerve of a patient, comprising:

providing a hyperechogenic stimulating block needle, said needle comprising an electrically conductive rigid shaft having a longitudinal axis, a proximal end, a distal end, and an outer surface extending from the proximal end to the distal end, said distal end including a tip portion defining a point; a hyperechogenic particulate material affixed to said shaft along at least a portion of the outer surface, said hyperechogenic particulate material operable in response to a beam of ultrasound waves in a two-dimensional ultrasound plane to produce an image of said needle when said needle is in a position forming a non-90° angle between the longitudinal axis and the direction of the ultrasound waves in the two-dimensional ultrasound plane, thereby enhancing the ultrasonic imaging characteristics of the needle; and a polymeric coating positioned over at least a portion of said shaft and covering said hyperechogenic particulate material, the polymeric coating having a lubricious external surface; wherein said hyperechogenic particulate material comprises a member selected from the group consisting of a particulate talc material, a particulate calcium-containing material, a silicate, a mineral including calcium, barium, aluminum or magnesium and a carbonate, sulfate, oxide, hydroxide or phosphate of calcium, magnesium, barium or aluminum;

inserting said tip portion into a patient;

aligning said tip portion in proximity with said nerve by visualization with two-dimensional ultrasound imaging and by electrical nerve stimulation; and injecting a local anesthetic drug through said lumen defined by said shaft into said patient.

40. The method of embodiment 39, wherein said electrical nerve stimulation comprises emitting an electrical pulse in a vicinity of said nerve, and adjusting an amount of current to elicit a motor response when said needle tip is advanced toward said nerve.

41. The method of embodiment 40, wherein said electrical pulse is emitted at from about 1 to about 2 Hz, and said current is adjusted at from about 1.0 to about 2.0 milliamps.

42. The method of embodiment 41, wherein said current is reduced as said needle tip approaches said nerve to a predetermined level prior to injection of said drug.

43. A method for making a needle for guided positioning in soft tissue of a patient with the aid of a real-time two-dimensional ultrasonic imaging apparatus, comprising:

providing a rigid shaft having a longitudinal axis and an outer surface;

applying to at least a portion of the outer surface a hyperechogenic particulate material comprising a member selected from the group consisting of a particulate talc material, a particulate calcium-containing material, a silicate, a mineral including calcium, barium, aluminum or magnesium and a carbonate, sulfate, oxide, hydroxide or phosphate of calcium, magnesium, barium or aluminum; and applying over at least a portion of said shaft a polymeric coating having a lubricious external surface.

44. The method of embodiment 43 wherein said applying a hyperechogenic particulate material and said applying a polymeric coating together comprise applying a mixture of the particulate material and a polymeric material to at least a portion of the outer surface as a single coating.

45. The method of embodiment 44, wherein the single coating is applied using a powder coating process.

46. The method of embodiment 43 wherein the hyperechogenic particulate material is operable in response to a beam of ultrasound waves in a two-dimensional ultrasound plane to produce an image of said needle when said needle is in a position forming a non-90° angle between the longitudinal axis and the direction of the ultrasound waves in the two-dimensional ultrasound plane, thereby enhancing the ultrasonic imaging characteristics of the needle.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least one", and "at least a portion" are not intended to limit the claims to only one item unless specifically stated to the contrary. Further, when the language "at least a portion" and/or "a portion" is used, the claims may include a portion and/or the entire item unless specifically stated to the contrary.

All publications mentioned herein are cited for the purpose of describing and disclosing the various features that are reported in the publications that might be used in connection with the embodiments described herein. Nothing herein is to be construed as an admission that the embodiments described herein are not entitled to antedate such disclosures by virtue of prior invention.

What is claimed is:

1. A needle effective for guided positioning in soft tissue of a patient with the aid of a real-time two-dimensional ultrasonic imaging apparatus, the needle comprising:
a rigid shaft having a longitudinal axis, a proximal end, a distal end, and an outer surface extending from the proximal end to the distal end, said distal end including a tip portion defining a point;
a hyperechogenic layer affixed to said shaft along at least a portion of the outer surface;
wherein said hyperechogenic layer comprises a polymeric material having a hyperechogenic particulate material dispersed therein;
wherein said hyperechogenic particulate material is operable in response to a beam of ultrasound waves in a two-dimensional ultrasound plane to produce an image of said needle when said needle is in a position forming a non-90° angle between the longitudinal axis and the direction of the ultrasound waves in the two-dimensional ultrasound plane; and
wherein said hyperechogenic particulate material comprises a particulate talc material.

2. The needle in accordance with claim 1 wherein said particulate talc material has an average particle size of from about 2 to about 18 microns.

3. The needle in accordance with claim 1 wherein said polymeric material comprises a thermoplastic polymer material.

4. The needle in accordance with claim 1 wherein said polymeric material comprises a member selected from the group consisting of polyurethane, polyethylene, nylon, polytetrafluoroethylene, polyvinyl chloride, polypropylene, polyester, parylene, silicone and polyethylene terephthalate.

5. A needle effective for guided positioning in soft tissue of a patient with the aid of a real-time two-dimensional ultrasonic imaging apparatus, the needle comprising:
a rigid shaft having a longitudinal axis, a proximal end, a distal end, and an outer surface extending from the proximal end to the distal end, said distal end including a tip portion defining a point;
a hyperechogenic particulate material affixed to said shaft along at least a portion of the outer surface, said hyperechogenic particulate material operable in response to a beam of ultrasound waves in a two-dimensional ultrasound plane to produce an image of said needle when said needle is in a position forming a non-90° angle between the longitudinal axis and the direction of the ultrasound waves in the two-dimensional ultrasound plane; and
a polymeric coating positioned over at least a portion of said shaft and covering said hyperechogenic particulate material, the polymeric coating having a lubricious external surface;
wherein said hyperechogenic particulate material comprises a particulate talc material.

6. The needle in accordance with claim 5 wherein said particulate talc material has an average particle size of from about 2 to about 18 microns.

7. The needle in accordance with claim 5 wherein said particulate talc material comprises platy talc.

8. The needle in accordance with claim 5 wherein said polymeric coating comprises polyethylene terephthalate.

9. The needle in accordance with claim 1 wherein said hyperechogenic particulate material further comprises a calcium-containing material.

10. The needle in accordance with claim 9 wherein said calcium-containing material comprises particulate calcium carbonate.

11. The needle in accordance with claim 10 wherein said particulate calcium carbonate comprises a member selected from the group consisting of ground calcium carbonate and precipitated calcium carbonate.

12. The needle in accordance with claim 9 wherein said calcium-containing material comprises a member selected from the group consisting of calcium phosphate and hydroxyapatite.

13. The needle in accordance with claim 5 wherein the particulate material is a surface coated particulate material.

14. The needle in accordance with claim 13 wherein the surface coated particulate material includes a stearic acid coating.

15. The needle in accordance with claim 5 wherein said shaft comprises surgical grade steel.

16. The needle in accordance with claim 5 wherein said shaft further includes an inner surface defining a lumen through said shaft.

17. The needle in accordance with claim 5 wherein at least a portion of said hyperechogenic particulate material is positioned between said shaft and said polymeric coating.

18. The needle in accordance with claim 5 wherein at least a portion of said hyperechogenic particulate material is dispersed in said polymeric coating.

19. The needle in accordance with claim 18 wherein said hyperechogenic particulate material is dispersed in said polymeric coating at a concentration of from about 5 to about 25 weight percent.

20. The needle in accordance with claim 5 wherein said needle comprises a friction lowering material affixed to said lubricious external surface.

21. The needle in accordance with claim 5
   wherein said needle is configured for use in blocking a nerve of a patient using simultaneous electrical nerve stimulation and two-dimensional ultrasound visualization of the nerve; and
   wherein said polymeric coating composes an insulating layer covering at least a portion of said shaft.

22. The needle in accordance with claim 21 wherein said polymeric coating covers at least a portion of said hyperechogenic particulate material.

23. The needle in accordance with claim 21 wherein said shaft is electrically conductive, said polymeric layer covers substantially all of said shaft except not said tip portion.

24. The needle in accordance with claim 21 wherein said shaft is electrically conductive, said polymeric layer covers substantially all of said shaft.

25. The needle in accordance with claim 21 wherein said polymeric coating comprises a member selected from the group consisting of polyurethane, polyethylene, nylon, polytetrafluoroethylene, polyvinyl chloride, polypropylene, polyester, parylene and silicone.

26. The needle in accordance with claim 21 wherein said polymeric coating comprises a polyethylene terephthalate.

27. The needle in accordance with claim 5 wherein said tip comprises a bevel.

* * * * *